(12) United States Patent
Takahasi et al.

(10) Patent No.: US 7,056,677 B2
(45) Date of Patent: Jun. 6, 2006

(54) SOLUBLE MAST CELL FUNCTION ASSOCIATED ANTIGEN (MAFA) PHARMACEUTICAL COMPOSITIONS AND METHODS OF MAKING AND USING THEM

(75) Inventors: Nobuaki Takahasi, Solana Beach, CA (US); Toshifumi Mikayama, San Diego, CA (US)

(73) Assignee: Gemini Science, Inc., San Diego, CA (US)

( * ) Notice: Subject to any disclaimer, the term of this patent is extended or adjusted under 35 U.S.C. 154(b) by 0 days.

(21) Appl. No.: 09/811,367

(22) Filed: Mar. 16, 2001

(65) Prior Publication Data

US 2002/0155110 A1 Oct. 24, 2002

Related U.S. Application Data

(60) Provisional application No. 60/190,716, filed on Mar. 17, 2000.

(51) Int. Cl.
*G01N 33/53* (2006.01)
*G01N 33/563* (2006.01)
*C07K 16/28* (2006.01)

(52) U.S. Cl. .................. 435/7.1; 435/7.2; 435/7.21; 530/350; 530/387.1; 530/388.22

(58) Field of Classification Search ............. 424/185.1, 424/134.1; 435/7.1, 7.21, 7.24, 7.2; 530/387.1, 530/388.22
See application file for complete search history.

(56) References Cited

U.S. PATENT DOCUMENTS 6,034,227 A  3/2000  Pecht et al.

FOREIGN PATENT DOCUMENTS

| WO | WO 95/27734 | 10/1995 |
|---|---|---|
| WO | WO 98/54209 | 12/1998 |

OTHER PUBLICATIONS

Kuby et al., 1994, Immunology, second edition, pp. 85-96.*
Ngo et al., 1994, The Protein Folding Problem and Tertiary Structure Prediction, pp. 492-495.*
J of Protein Chemistry 11(5): 433-444, 1992.*
Sota, et al., "A Monoclonal Antibody That Inhibits Secretion from Rat Basophilic Leukemia Cells and Binds to a Novel Membrane Component", The Journal of Immunology, vol. 141, 4324-4332, No. 12, Dec. 15, 1988.
Guthmann et al., "A Secretion Inhibitory Signal Transduction Molecule on Mast Cells is Another C-type Lectin", Proc. Natl. Acad. Sci., USA vol. 92, pp. 9397-9401, Sep. 1995.
Butoner, et al., MAFA-L, an ITIM-containing Receptor Encoded By The Human NK Cell Gene Complex and Expressed By Basophils and NK Cells, Eur. J. Immunol., 1998, 28: 3755-3762.
Hanke, et al., 2F1 Antigen, The Mouse Homolog of the Rat "Mast Cell Function-Associated Antigen", is a Lectin-like Type II Transmembrane Receptor Expressed By Natural Killer Cells, Eur. J. Immunol., 1998, 28: 4409-4417.
Blaser, et al., Cutting Edge: Virus-Activated CD8 T Cells and Lymhokine-Activated NK Cells Express the Mast Cell Function-Associated Antigen, An Inhibitory C-Type Lectin, The American Association of Immunologists, 1998, 161:6451-6454.
Corral, et al., NK Cell Expression of the Killer Cell Lectin-like Receptor G1 (KLRG1), The Mouse Homolog of MAFA, is Modulated by MHC Class 1 Molecules, Eur. J. Immunol. 2000, 30: 920-930.

* cited by examiner

*Primary Examiner*—Christina Chan
*Assistant Examiner*—Phuong N Huynh
(74) *Attorney, Agent, or Firm*—Pillsbury Winthrop Shaw Pittman LLP

(57) ABSTRACT

This invention provides pharmaceutical compositions and methods for controlling and modifying Natural Killer (NK) cell and T cell functions by manipulation of "mast cell function-associated antigen," or "MAFA," polypeptide-mediated cell signaling. The invention provides a pharmaceutical compositions and methods using an agent that specifically binds to an MAFA ligand on a target cell and prevents or inhibits NK- or T cell-expressed cell surface MAFA from binding to the MAFA ligand on the target cell. Preventing or inhibiting an NK- or a T cell-expressed cell surface MAFA from binding to the MAFA ligand on the target cell prevents or inhibits the cell surface MAFA from generating an inhibitory signal to the NK or the T cell. The invention also provides pharmaceutical compositions and methods using an agent that specifically binds to an NK- or a T cell-expressed cell surface MAFA and prevents or inhibits the NK- or T cell-expressed cell surface MAFA from binding to a MAFA ligand or generating an inhibitory signal to the NK or the T cell. The invention also provides pharmaceutical compositions and methods using an agent that specifically binds to an NK- or a T cell-expressed cell surface MAFA and inhibits an NK cell or T cell activity.

2 Claims, 8 Drawing Sheets

SEQUENCE LISTING

<160> NUMBER OF SEQ ID NOS: 20

<210> SEQ ID NO 1
<211> LENGTH: 189
<212> TYPE: PRT
<213> ORGANISM: Homo sapiens

<400> SEQUENCE: 1

```
Met Thr Asp Ser Val Ile Tyr Ser Met Leu Glu Leu Pro Thr Ala Thr
1               5                   10                  15

Gln Ala Gln Asn Asp Tyr Gly Pro Gln Gln Lys Ser Ser Ser Ser Lys
            20                  25                  30

Pro Ser Cys Ser Cys Leu Val Ala Ile Thr Leu Gly Leu Leu Thr Ala
        35                  40                  45

Val Leu Leu Ser Val Leu Leu Tyr Gln Trp Ile Leu Cys Gln Gly Ser
    50                  55                  60

Asn Tyr Ser Thr Cys Ala Ser Cys Pro Ser Cys Pro Asp Arg Trp Met
65                  70                  75                  80

Lys Tyr Gly Asn His Cys Tyr Tyr Phe Ser Val Glu Glu Lys Asp Trp
                85                  90                  95

Asn Ser Ser Leu Glu Phe Cys Leu Ala Arg Asp Ser His Leu Leu Val
            100                 105                 110

Ile Thr Asp Asn Gln Glu Met Ser Leu Leu Gln Val Phe Leu Ser Glu
        115                 120                 125

Ala Phe Cys Trp Ile Gly Leu Arg Asn Asn Ser Gly Trp Arg Trp Glu
    130                 135                 140

Asp Gly Ser Pro Leu Asn Phe Ser Arg Ile Ser Ser Asn Ser Phe Val
```

```
                145                 150                 155                 160
Gln Thr Cys Gly Ala Ile Asn Lys Asn Gly Leu Gln Ala Ser Ser Cys
                    165                 170                 175
Glu Val Pro Leu His Gly Val Cys Lys Lys Val Arg Leu
                180                 185

<210> SEQ ID NO 2
<211> LENGTH: 570
<212> TYPE: DNA
<213> ORGANISM: Homo sapiens

<400> SEQUENCE: 2
atgactgaca gtgttatttta ttccatgtta gagttgccta cggcaaccca agcccagaat      60
gactacggac cacagcaaaa atcttcctct tccaagcctt cttgttcttg ccttgtggca     120
ataactttgg ggcttctgac tgcagttctt ctgagtgtgc tgctatacca gtggatcctg     180
tgccagggct ccaactactc cacttgtgcc agctgtccta gctgcccaga ccgctggatg     240
aaatatggta accattgtta ttatttctca gtggaggaaa aggactggaa ttctagtctg     300
gaattctgcc tagccagaga ctcacacctc cttgtgataa cggacaatca ggaaatgagc     360
ctgctccaag ttttcctcag tgaggccttt tgctggattg gtctgaggaa caattctggc     420
tggaggtggg aagacggatc acctctaaac ttctcaagga tttcttctaa tagctttgtg     480
cagacatgcg gtgccatcaa caaaaatggt cttcaagcct caagctgtga agttccttta     540
cacggggtgt gtaagaaggt cagactttga                                      570

<210> SEQ ID NO 3
<211> LENGTH: 188
<212> TYPE: PRT
<213> ORGANISM: Mus musculus

<400> SEQUENCE: 3

Met Ala Asp Ser Ser Ile Tyr Ser Thr Leu Glu Leu Pro Glu Ala Pro
1               5                   10                  15

Gln Val Gln Asp Glu Ser Arg Trp Lys Leu Lys Ala Val Leu His Arg
            20                  25                  30

Pro His Leu Ser Arg Phe Ala Met Val Ala Leu Gly Leu Leu Thr Val
        35                  40                  45

Ile Leu Met Ser Leu Leu Met Tyr Gln Arg Ile Leu Cys Cys Gly Ser
    50                  55                  60

Lys Asp Ser Thr Cys Ser His Cys Pro Ser Cys Pro Ile Leu Trp Thr
65                  70                  75                  80

Arg Asn Gly Ser His Cys Tyr Tyr Phe Ser Met Glu Lys Lys Asp Trp
                85                  90                  95

Asn Ser Ser Leu Lys Phe Cys Ala Asp Lys Gly Ser His Leu Leu Thr
            100                 105                 110

Phe Pro Asp Asn Gln Gly Val Lys Leu Phe Gly Glu Tyr Leu Gly Gln
        115                 120                 125

Asp Phe Tyr Trp Ile Gly Leu Arg Asn Ile Asp Gly Trp Arg Trp Glu
    130                 135                 140

Gly Gly Pro Ala Leu Ser Leu Arg Ile Leu Thr Asn Ser Leu Ile Gln
145                 150                 155                 160

Arg Cys Gly Ala Ile His Arg Asn Gly Leu Gln Ala Ser Ser Cys Glu
                165                 170                 175

Val Ala Leu Gln Trp Ile Cys Lys Lys Val Leu Tyr
            180                 185
```

<210> SEQ ID NO 4
<211> LENGTH: 997
<212> TYPE: DNA
<213> ORGANISM: Mus musculus

<400> SEQUENCE: 4

```
gtccctcatg gtgtttctca ccccacttac agcccacatt ccccactgag tgtgaaaggg      60
atttggtaga gatggctgac agctctatct attcaacact agagctgccg gaggcacctc     120
aagtccaaga tgagtccaga tggaagctca aagctgtctt acaccggccc catctttccc     180
gctttgcaat ggtggctttg ggcttttga  ctgtgattct catgagtcta ctgatgtatc     240
aacggatcct gtgctgcggc tccaaggact ctacatgttc ccactgcccc agctgcccca     300
tcctctggac gaggaatggt agccactgtt actattttc  aatggagaaa aaggactgga     360
attctagtct gaaattctgt gcagacaaag gctcacatct ccttacatt  ccggacaacc     420
agggagtgaa gctgtttgga gagtacctgg gtcaggactt ttactggatc ggcttgagga     480
acattgatgg ctggaggtgg aaggcggcc  cagcgctcag cttgaggatt cttaccaaca     540
gcttgataca gaggtgcggt gccattcaca gaaatggcct ccaagcctcc agttgtgaag     600
ttgctttgca gtggatctgt aagaaggtcc tatactgatg gatgccactg tgtcctgagc     660
ctcggatctg ccacatgtgt ttaaaaagag ggaatgggtc tggggaatct tgtctacaa      720
atgtgtgttt aacaaatgcc aaacctgtta tgatatgcca ttagacagag gattagcata     780
cctttctggg ggttggcctt ttcctgttgg gcttttccg  cgactgttta agtattaggc     840
tagccattta aagcctaaat ctgggcaaat caaatgataa agcttattta atggataccc     900
accctgcaga tagccaccct ggctctctca tccttcctct gccatctctg tcaagagaga     960
gaaactatca tcctcagaga tgaccctgcg catcaga                              997
```

<210> SEQ ID NO 5
<211> LENGTH: 188
<212> TYPE: PRT
<213> ORGANISM: Rattus norvegicus

<400> SEQUENCE: 5

```
Met Ala Asp Asn Ser Ile Tyr Ser Thr Leu Glu Leu Pro Ala Ala Pro
1               5                   10                  15

Arg Val Gln Asp Asp Ser Arg Trp Lys Val Lys Ala Val Leu His Arg
            20                  25                  30

Pro Cys Val Ser Tyr Leu Val Met Val Ala Leu Gly Leu Leu Thr Val
        35                  40                  45

Ile Leu Met Ser Leu Leu Leu Tyr Gln Arg Thr Leu Cys Cys Gly Ser
    50                  55                  60

Lys Gly Phe Met Cys Ser Gln Cys Ser Arg Cys Pro Asn Leu Trp Met
65                  70                  75                  80

Arg Asn Gly Ser His Cys Tyr Tyr Phe Ser Met Glu Lys Arg Asp Trp
                85                  90                  95

Asn Ser Ser Leu Lys Phe Cys Ala Asp Lys Gly Ser His Leu Leu Thr
            100                 105                 110

Phe Pro Asp Asn Gln Gly Val Asn Leu Phe Gln Glu Tyr Val Gly Glu
        115                 120                 125

Asp Phe Tyr Trp Ile Gly Leu Arg Asp Ile Asp Gly Trp Arg Trp Glu
    130                 135                 140

Asp Gly Pro Ala Leu Ser Leu Ser Ile Leu Ser Asn Ser Val Val Gln
```

```
            145                 150                 155                 160
Lys Cys Gly Thr Ile His Arg Cys Gly Leu His Ala Ser Ser Cys Glu
                165                 170                 175

Val Ala Leu Gln Trp Ile Cys Glu Lys Val Leu Pro
            180                 185

<210> SEQ ID NO 6
<211> LENGTH: 1461
<212> TYPE: DNA
<213> ORGANISM: Rattus norvegicus

<400> SEQUENCE: 6
caccctgctt actgtcgtca ctccctgctg agtgtgaagg gcgttgggtg gagatggccg      60
acaactctat ctactcaaca ttagagctgc ctgctgcacc tcgagtccaa gatgactcca     120
gatggaaggt caaagctgtc ttacaccgac cctgtgtttc ctaccttgtg atggtggctt     180
tggggctttt gactgtgatt ctcatgagtc tactgttgta ccaacggact ctgtgctgtg     240
gctccaaggg ctttatgtgt tcccagtgct ccaggtgccc caacctctgg atgaggaacg     300
ggagccactg ttactacttc tcaatggaga aagggactg gaactctagt ctgaagttct     360
gtgcagacaa aggctcgcat ctccttacat ttccggacaa ccagggagtg aacctgttcc     420
aggagtatgt gggcgaggac ttttactgga ttggcttgag ggacatcgat ggctggaggt     480
gggaagatgg cccagctctc agcttaagca ttctctctaa cagcgtggta cagaagtgtg     540
gcaccatcca caggtgtggc ctccacgcct ccagttgtga ggttgctttg cagtggatct     600
gtgagaaggt cctgccctga aggattccac tgtgtcccaa gcctcagatc tgccacatgt     660
cttcaaaaag agggaatggg catggggaac ctctgttcac aaaggtgtct ttagcaaatg     720
ccaaacctgt tatgatatgc cattagacag gcgttagcat tccttcctgg gagctggcat     780
ttttcaactg gctttctcag tcatgttag ccatttaaag cctaaatctg gcaaatgaa      840 atagataaaa tttattttga tggctcttac tgcacaaact caccctggct ttctcatccc     900
atactctgcc atatctatca agatatgtg caaaactatt catctgcaga gaaccccca      960 ccacggtcaa taacacatta catagacatc gaatagagac agaaaagcaa acacctcctg    1020
ttctcactcc tgcttggaag ctgaagtagc tcaagcctga ggtgtaggga gaagtgcagt    1080
ggttaccaga gtccaggaga ctgaagggat ggtagaggtt ggttaatggt ttggctggtg    1140
tggggtgacc atcatgatta atgattgttg tatgtttgcc aatatgttgt gaacttccgg    1200
atagcgaggt ggaaggaccg tgggtgttac caaatgcctg caggagagat gtgctgagaa    1260
ccctgactgg atgatttcca cacacattga aatatcacac tgtgccccat aaatgtgtac    1320
aatcattatc tatccctaat ttccctaaaa attaaagaag tcccaattaa aataaaaaat    1380
acctttctgc taaaaaaaaa aaaaaaaaa aaaaaaaaa aaaaaaaaa aaaaaaaaa        1440 aaaaaaaaaa aaaaaaaaa a                                                1461

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 7
ccttgtgatg gtggctttgg ggcttttgac tg                                    32
```

```
<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 8
actgcaaagc aacctcacaa ctggaggc                                    28

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 9
atatggatcc tccaaggact ctacatgttc                                  30

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 10
atatgcggcc gctcagtata ggaccttctt acag                             34

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence:Primer

<400> SEQUENCE: 11
cccggatccg catcaccatc accatcacgc ggccgcttcc aaggactcta catgttccca 60
ctgc                                                              64

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 12
atatgcggcc gctcagtata ggaccttctt acag                             34

<210> SEQ ID NO 13
<211> LENGTH: 73
<212> TYPE: DNA
<213> ORGANISM: Artificial Sequence
<220> FEATURE:
<223> OTHER INFORMATION: Description of Artificial Sequence:Primer

<400> SEQUENCE: 13
cccaagctta caaccatggc tgaccgctct atcgcctcaa cagccgagct gccggaggca 60
cctcaagtcc aag                                                    73

<210> SEQ ID NO 14
<211> LENGTH: 66
<212> TYPE: DNA
```

<213> ORGANISM: Artificial Sequence
<220> FEATURE:
<223> OTHER INFORMATION: Description of Artificial Sequence:Primer

<400> SEQUENCE: 14
cccctcgagc tacagatcct cttcagagat gagtttctgc tcgtatagga ccttcttaca    60
gatcca    66

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 15
cgacaactct atctactcaa cactagagct gc    32

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 16
cacagaattt cagactcgag ttccagtcct t    31

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 17
actggaactc gagtctgaaa ttctgtgcag    30

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 18
ggatgaattc cccgtatagg accttcttac ag    32

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 19
acgaattcac aaccatggcc gacaactcta tctac    35

<210> SEQ ID NO 20
<211> LENGTH: 32
<212> TYPE: DNA
<213> ORGANISM: Artificial Sequence
<220> FEATURE:

-continued

```
<223> OTHER INFORMATION: Description of Artificial Sequence:Primer

<400> SEQUENCE: 20
ggatgaattc cccgtatagg accttcttac ag                                32
```

US 7,056,677 B2

SOLUBLE MAST CELL FUNCTION ASSOCIATED ANTIGEN (MAFA) PHARMACEUTICAL COMPOSITIONS AND METHODS OF MAKING AND USING THEM

This application claims priority to Provisional Application Ser. No. 60/190,716, filed Mar. 17, 2000.

TECHNICAL FIELD

This invention generally pertains to the fields of cell biology, immunology and medicine. In particular, this invention provides pharmaceutical compositions and methods for controlling and modifying Natural Killer (NK) cell and T cell functions by manipulation of "mast cell function-associated antigen," or "MAFA," polypeptide-mediated cell signaling and ligand binding.

BACKGROUND

Current approaches to immune therapy for cancer and infectious diseases are limited. Several biological mechanisms may account for the inability to achieve adequate immune protection. It has been postulated that the inhibition of the cytotoxic function of anti-tumor cells, such as NK cells or T cells, by their target cells (e.g., tumor cells) may play a role in this inability. The discovery of new methods and pharmaceuticals capable of allowing the body to bypass or to block this target (tumor)-cell mediated immune inhibition would provide an important new ways to treat cancer and other diseases and conditions.

In contrast, activation of NK cell or T cell cytotoxic function can be a major obstacle to the success of allogenic transplantations, including graft and organ transplants. Activation of these cells may have a pathological role in autoimmune diseases as well. Thus, the discovery of new methods and pharmaceuticals to negatively regulate the cytolytic activity of NK or T cells would provide important means to ameliorate or block these unwanted responses by the immune system.

"Mast cell function-associated antigen," or "MAFA," was originally identified using a monoclonal antibody that inhibited rat mast cell activation in the presence of IgE. Cross-linking of cell surface MAFA inhibited IgE-stimulated mast cell degranulation (see, e.g., Ortega (1988) J. Immunol. 141:4324–4332). Cloning of the rat MAFA gene identified a type II membrane glycoprotein expressed on the surface of basophilic mast cells (see, e.g., Guthmann (1995) Proc. Natl. Acad. Sci. USA 92:9397–9401). Initially, it was believed that expression of the MAFA gene was limited to mast cells (see, e.g., Bocek (1997) J. Immunol. 158(7):3235–3243). More recently, MAFA was also found to be expressed by NK cells and virus-activated cytotoxic T cells (see, e.g., Hanke (1998) Eur. J. Immunol. 28:4409–17; Butcher (1998) Eur. J. Immunol. 28:3755–3762; Blaser (1998) J. Immunol. 161: 6451–6454).

While cross linking of cell surface MAFA (by anti-MAFA antibodies) inhibited IgE-stimulated mast cell degranulation, Hanke (1998) Eur. J. Immunol. 28(12):4409–4417, reported that a monoclonal antibody against murine MAFA failed to show either stimulatory or inhibitory activity in various NK cell cytotoxic assays against a large number of different tumor and lymphoblast target cells. Therefore, it remained unclear whether MAFA was involved in the regulation of NK cell functions.

SUMMARY

The invention provides a pharmaceutical composition comprising an agent that specifically binds to a MAFA ligand on a target cell and prevents or inhibits NK- or T cell-expressed cell surface MAFA from binding to the MAFA ligand on the target cell, and a pharmaceutically acceptable excipient. In one embodiment, the pharmaceutical composition, by preventing or inhibiting an NK- or a T cell-expressed cell surface MAFA from binding to the MAFA ligand on a target cell, prevents or inhibits the cell surface MAFA from generating an inhibitory signal to the NK or the T cell. By preventing or inhibiting the cell surface MAFA-generated inhibitory signal, the pharmaceutical composition can stimulate an NK cell or a T cell activity. In an alternative embodiment, stimulated NK cell activity is an increase in NK cell- or T cell-mediated cell killing, such as an increase in NK cell or T cell-mediated tumor cell killing. The pharmaceutical composition-stimulated T cell activity can be an increase in T killer cell (CTL) activity, an increase in CTL activity against virally infected cells or cytokine secretion by the T cell.

In one embodiment, the pharmaceutical composition's agent that specifically binds to the NK- or the T cell-expressed cell surface MAFA ligand comprises a soluble MAFA polypeptide. The soluble MAFA polypeptide can comprise the extracellular domain of a MAFA polypeptide, such as a soluble human MAFA polypeptide. The MAFA polypeptide of the pharmaceutical composition can be a soluble human MAFA polypeptide comprising a sequence from about amino acid residue 64 to about amino acid residue 189 of SEQ ID NO:1, or an equivalent thereof.

The invention also provides kits comprising a pharmaceutical composition comprising a soluble MAFA polypeptide capable of specifically binding to a MAFA ligand on a target cell, and a pharmaceutically acceptable excipient; and printed matter comprising instructions for using the pharmaceutical composition to stimulate an NK cell or a T cell activity or to treat an NK cell- or T cell-susceptible disease or condition (e.g., a tumor) or to identify an NK or a T cell target. In one embodiment, the stimulated NK cell- or T cell-activity is an increase in NK cell- or T cell-mediated cell killing, such as NK cell- or T cell-mediated tumor cell killing. In alternative embodiments, the stimulated T cell activity is an increase in T killer cell (CTL) activity, an increase in CTL activity against virally infected cells or cytokine secretion by the T cell or an initiation.

The invention also provides pharmaceutical compositions comprising an agent that specifically binds to an NK- or a T cell-expressed cell surface MAFA and prevents or inhibits the NK- or T cell-expressed cell surface MAFA from binding to a MAFA ligand, and a pharmaceutically acceptable excipient.

The invention also provides a pharmaceutical composition comprising an agent that specifically binds to an NK- or a T cell-expressed cell surface MAFA and prevents or inhibits the NK- or T cell-expressed cell surface MAFA from generating an inhibitory signal to the NK or the T cell, and a pharmaceutically acceptable excipient. The pharmaceutical composition, by preventing or inhibiting the NK- or T cell-expressed cell surface MAFA from generating an inhibitory signal to the NK or the T cell, can stimulate an NK cell or a T cell activity. In one embodiment, the stimulated NK cell or T cell activity is an increase in NK cell or T cell-mediated cell killing, such as an increase in NK cell or T cell-mediated tumor cell killing. In alternative embodiment, the stimulated T cell activity is an increase in T killer cell (CTL) activity, cytokine secretion by the T cell, or an increase in T killer cell (CTL) activity against virally infected cells.

In one embodiment, the pharmaceutical composition's agent that specifically binds to the NK- or the T cell-expressed cell surface MAFA can be an anti-MAFA antibody, including fragments, or subsequences, of an anti-MAFA antibody, or equivalents thereof, comprising an antigen binding site.

The invention also provides a kit comprising a pharmaceutical composition comprising an antibody that specifically binds to an NK- or a T cell-expressed cell surface MAFA or a composition comprising a subsequence of an anti-MAFA antibody, wherein the subsequence comprises an antigen binding site that specifically binds to an NK- or a T cell-expressed cell surface MAFA, and a pharmaceutically acceptable excipient, wherein the antibody binding to the NK- or T cell-expressed cell surface MAFA prevents or inhibits the MAFA from generating an inhibitory signal to the NK or the T cell; and, printed matter comprising instructions for using the pharmaceutical composition, wherein the instructions indicate use of the pharmaceutical composition to stimulate an NK cell or a T cell activity. In alternative embodiment of the kit, the instructions indicate use of the pharmaceutical composition to increase NK cell or T cell mediated cell killing, such as increasing NK cell- or T cell-mediated tumor cell killing, to increase T killer cell (CTL) activity or to increase cytokine secretion by the T cell. The increased CTL activity can be an increased CTL activity to virally infected cells.

The invention also provides a pharmaceutical composition comprising an agent that specifically binds to an NK- or a T cell-expressed cell surface MAFA to generate an inhibitory signal to the NK or the T cell, and a pharmaceutically acceptable excipient. In one embodiment, generating the inhibitory signal to the NK or the T cell prevents or inhibits an NK cell or a T cell activity. In alternative embodiments, the inhibited NK cell or T cell activity is a decrease in NK cell- or T cell-mediated cell killing, such as a decrease in NK cell- or T cell-mediated tumor cell killing. The pharmaceutical composition-inhibited T cell activity can be a decrease in T killer cell (CTL) activity or cytokine secretion by a T cell. The pharmaceutical composition-inhibited NK cell or T cell activity can be a decreased or inhibited allogenic response or graft or transplant rejection reaction or inhibition of an autoimmune reaction or disease.

In one embodiment, the inhibitory signal-generating pharmaceutical composition's agent can be an anti-MAFA antibody. The anti-MAFA antibody can be an antibody that specifically binds to human MAFA. The anti-MAFA antibody can have the same antigen binding specificity as an antibody produced by a hybridoma designated as 7B5 or, the anti-MAFA antibody can be produced by a hybridoma designated as 7B5. In alternative embodiments, the anti-MAFA antibody is an antibody that specifically binds to human MAFA, the anti-MAFA antibody has the same antigen binding specificity as an antibody produced by a hybridoma designated as 1F10, and, the anti-MAFA antibody can be produced by a hybridoma designated as 1F10.

The invention provides a kit comprising a pharmaceutical composition comprising an antibody that specifically binds to an NK- or a T cell-expressed cell surface MAFA and a pharmaceutically acceptable excipient, wherein the antibody binding to the NK- or T cell-expressed cell surface MAFA generates an inhibitory signal to the NK or the T cell; and, printed matter comprising instructions for using the pharmaceutical composition, wherein the instructions indicate use of the pharmaceutical composition to inhibit an NK cell or a T cell activity. In one embodiment, the instructions indicate use of the pharmaceutical composition to inhibit an NK cell activity. The inhibited NK cell activity can be a decrease or inhibition of allogenic reactions or graft or transplant rejections or to inhibit autoimmune disease. In alternative embodiments, the instructions indicate use of the pharmaceutical composition to inhibit T killer cell (CTL) activity, to inhibit cytokine secretion by the T cell, to decrease or inhibit graft or transplant rejections, or to inhibit autoimmune reaction or disease.

In one embodiment, the kit's pharmaceutical compositions' agent that specifically binds the NK cell or the T cell-expressed cell surface MAFA is an anti-MAFA antibody or a composition comprising a subsequence of an anti-MAFA antibody, wherein the subsequence comprises an antigen binding site.

The invention provides a method for inhibiting an NK- or a T cell-expressed cell surface MAFA binding to a ligand on a target cell comprising the following steps: (a) providing a soluble agent that prevents the binding of the NK- or the T cell-expressed cell surface MAFA to its target cell ligand; and (b) contacting the soluble agent to the NK or the T cell or the target cell in an amount sufficient to inhibit cell surface MAFA binding to the ligand on the target cell. In one embodiment, the soluble agent that prevents the binding of the NK- or the T cell-expressed cell surface MAFA to its target cell ligand is an anti-MAFA antibody, or a composition comprising a subsequence of an anti-MAFA antibody, wherein the subsequence comprises an antigen binding site, that binds to the cell surface MAFA.

In one embodiment of the method, the soluble agent that prevents the binding of the NK- or the T cell-expressed cell surface MAFA polypeptide to its target cell ligand is a soluble MAFA polypeptide that binds to the target cell ligand. In alternative embodiments, the soluble MAFA polypeptide is a human MAFA polypeptide, the extracellular domain of a MAFA polypeptide, a soluble MAFA polypeptide can comprise a sequence from about amino acid residue 64 to about amino acid residue 189 of SEQ ID NO:1, or equivalents thereof.

In alternative embodiments of the method, the contacting is in vitro or ex vivo or in vivo. The in vivo contacting can comprise administering the soluble agent to a subject, such as a mammal, which can be a human. In one embodiment of the method, the target cell is a tumor cell.

In one embodiment of the method, inhibiting the NK- or the T cell-expressed cell surface MAFA binding to the ligand on the target cell prevents or inhibits the NK- or T cell-expressed cell surface MAFA from generating an inhibitory signal to the NK or the T cell. In one embodiment, preventing or inhibiting the NK- or T cell-expressed cell surface MAFA from generating an inhibitory signal to the NK or the T cell stimulates an activity of the NK or the T cell. The stimulated NK cell or T cell activity can be an increase in NK cell- or T cell-mediated cell killing. The stimulated NK cell- or T cell-mediated cell killing can be tumor cell killing. The method stimulated T cell activity an be an increase in T killer cell (CTL) activity or cytokine secretion by the T cell or an increase in T killer cell (CTL) activity against virally infected cells.

The invention provides a method for treating a tumor by stimulating the cytotoxic activity of an NK cell or a cytotoxic T cell (CTL), wherein the tumor comprises an NK cell- or CTL-susceptible tumor cell, comprising the following steps: (a) providing a soluble MAFA polypeptide that binds to an NK- or CTL-expressed cell surface MAFA ligand expressed on the tumor cell or an antibody or a composition comprising a subsequence of an anti-MAFA antibody, wherein the subsequence comprises an antigen binding site, that binds to an NK- or CTL-expressed cell surface MAFA; and (b) administering the soluble MAFA polypeptide or anti-MAFA antibody in an amount sufficient to prevent binding of the NK- or CTL-expressed cell surface MAFA to its ligand on the tumor cell and to stimulate the cytotoxic activity of the NK or T cell to the tumor cell.

The invention provides a method for inhibiting an activity of an NK cell or a T cell comprising the following steps: (a) providing an antibody, or, a composition comprising a subsequence of an anti-MAFA antibody, wherein the subsequence comprises an antigen binding site, that binds to an NK- or CTL-expressed cell surface MAFA; and, (b) administering the anti-MAFA antibody in an amount sufficient to inhibit an activity of the NK cell or the T cell. In one embodiment, the inhibited NK cell or T cell activity is cell killing by the NK cell or the T cell. In another embodiment, inhibiting NK cell activity delays or inhibits a graft or transplant rejection or an allogenic response or ameliorates an autoimmune disease. In one embodiment, inhibiting the T cell activity delays or inhibits a graft or transplant rejection or an allogenic response or ameliorates an autoimmune disease.

In one embodiment, the inhibited the anti-MAFA antibody is an antibody that specifically binds to human MAFA. In alternative embodiments, the anti-MAFA antibody has the same antigen binding specificity as an antibody produced by a hybridoma designated as 7B5; the anti-MAFA antibody is produced by a hybridoma designated as 7B5; the anti-MAFA antibody is an antibody that specifically binds to human MAFA, and the anti-MAFA antibody has the same antigen binding specificity as an antibody produced by a hybridoma designated as 1F10; and, the anti-MAFA antibody is produced by a hybridoma designated as 1F10.

The details of one or more embodiments of the invention are set forth in the accompanying drawings and the description below. A further understanding of the nature and advantages of the present invention is realized by reference to the remaining portions of the specification, the figures and claims.

All publications, GenBank deposited sequences, ATCC deposits, patents and patent applications cited herein are hereby expressly incorporated by reference for all purposes.

DESCRIPTION OF DRAWINGS

FIG. 5A (upper panel) shows the result when the anti-MAFA antibodies were used at a concentration of 5 ug/ml, while FIG. 5B (lower panel) shows the result when the anti-MAFA antibodies were used at a concentration of 0.5 ug/ml.

Like reference symbols in the various drawings indicate like elements.

DETAILED DESCRIPTION

Figure 1A:
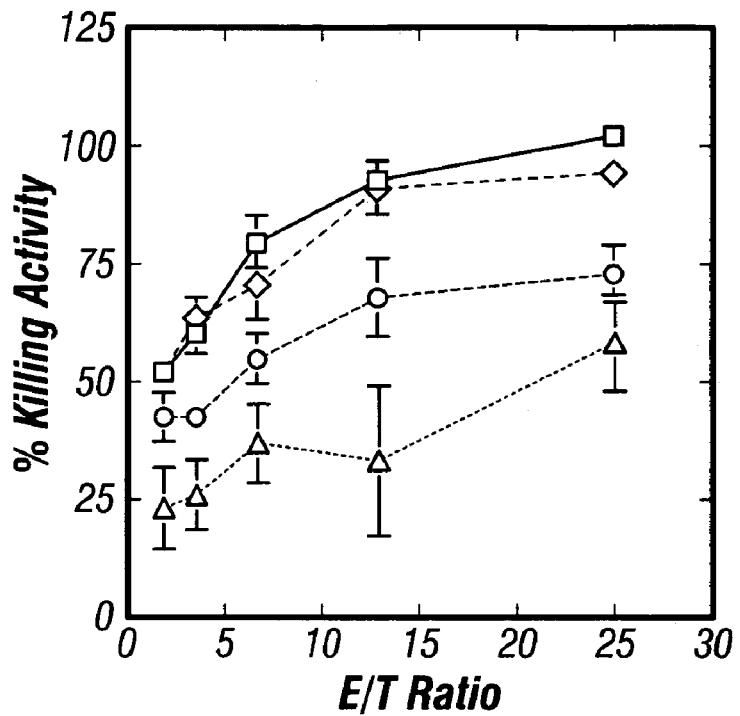
FIGS. 1A and 1B are graphs summarizing data showing the effect of F(ab')2 fragments of monoclonal antibodies 7B5 and 1F10 on the percent killing activity of NK cells against YAC-1 cells as a function of effector to target cell (E/T) ratio, as described in detail in Example 1. Concentrations of 5 ug/ml (FIG. 1A), and 0.5 ug/ml (FIG. 1B) F(ab')2, were used with PBS (square), F(ab')2 from normal rat IgG (lozenge), 1F10 (circle), 7B5 (triangle).

The invention provides pharmaceutical compositions and methods for inhibiting and stimulating Natural Killer (NK) cell and T cell function through the manipulation of "mast cell function-associated antigen," or "MAFA," polypeptide-mediated cell signaling. The invention for the first time demonstrates the use of compositions (e.g., pharmaceuticals) to manipulate MAFA functions, e.g., cytotoxic or secretory activity, of NK cells and T cells, such as cytotoxic T cells (CTLs).

While not limited by any particular functional mechanism or aspect of cell physiology, the pharmaceutical compositions and methods of the invention can be used to stimulate NK cell and T cell activities by decreasing (as in affinity) or inhibiting (e.g., blocking) the ability of cell surface expressed MAFA polypeptide to interact with a ligand expressed on a target cell. The pharmaceutical compositions and methods of the invention can be used to stimulate NK cell and T cell activities by interfering with or inhibiting the ability of cell surface expressed MAFA polypeptide to transmit inhibitory signals to these cells. The interference or blocking of the inhibitory signal to the cell by MAFA by use of the compositions of the invention can be linked to their ability to decrease or inhibit the ability of the cell surface expressed MAFA polypeptide to interact with its ligand (which typically is expressed on an NK or T cell target cell surface). Thus, by blocking or decreasing ("antagonizing") the MAFA-mediated inhibitory signal, the compositions and methods of the invention can be used to stimulate (i.e., block the inhibition of) NK and T cell activities.

The invention incorporates two strategies to effect this "antagonist" (of an inhibitory signal) effect. In one embodiment, the pharmaceuticals and methods of the invention comprise compositions, e.g., soluble MAFA polypeptides, that specifically bind to an NK cell or a T cell target to inhibit or block the ability of an NK or T cell surface-expressed MAFA to interact with the target in a manner that results in transmission of an inhibitory signal to the NK cell or T cell. The soluble MAFA can be any soluble fragment, or equivalent thereof, of a cell surface expressed MAFA having the ability to recognize a MAFA ligand on a target cell. In another embodiment, the pharmaceuticals and methods of the invention comprise compositions that specifically recognize an NK or T cell surface-expressed MAFA to inhibit or block the ability of an NK or T cell surface-expressed MAFA to transmit an inhibitory signal to the NK cell or T cell. The "antagonist" composition can be any molecule, including, e.g., a MAFA-binding polypeptide or peptide, including, e.g., an antibody or antibody fragment comprising a MAFA binding site.

Also while not limited by any particular functional mechanism or aspect of cell physiology, the pharmaceutical compositions and methods of the invention can be used to inhibit or block NK cell and T cell activities by mimicking the binding of a cell surface expressed MAFA polypeptide interaction with a ligand expressed on a target cell. The pharmaceutical compositions and methods of the invention can be used to inhibit NK cell and T cell activities by initiating or augmenting or stimulating the ability of cell surface expressed MAFA polypeptide to transmit inhibitory signals to these cells. The augmentation (in strength or duration) or initiation of the inhibitory signal to the cell by use of the compositions of the invention can be linked to their ability to imitate the result of the cell surface expressed MAFA polypeptide interaction with its ligand. Thus, by acting as an "agonist" of the MAFA-mediated inhibitory signal, the compositions and methods of the invention can be used to inhibit NK and T cell activities.

To generate this "agonist" effect, in one embodiment the invention uses compositions that specifically recognize an NK or T cell surface-expressed MAFA to generate an inhibitory signal to the NK or the T cell. The "agonist" composition can be any molecule, including, e.g., a MAFA-binding polypeptide or peptide, including, e.g., an antibody or antibody fragment comprising a MAFA binding site.

As described in Example 1, below, soluble recombinant murine MAFA and rat anti-mouse MAFA monoclonal antibodies were used to modify the function of MAFA-expressing NK cells and T cells, particularly cytotoxic lymphocytes (CTLs). The anti-MAFA antibodies of the invention strongly inhibited the cytotoxic activity of mouse NK cells and CTLs. In contrast, soluble MAFA significantly enhanced NK cell cytotoxic activity. It was also found that peptide-induced CTL express MAFA as well. These results demonstrate that MAFA polypeptide plays a role in the regulation of NK cell and T cell (e.g., CTL) activities, e.g., cytolytic activity or cytokine secretion. Accordingly, use of anti-MAFA antibodies that inhibit NK and/or CTL function can be used therapeutically to ameliorate or prevent conditions or diseases caused by NK or T cells, e.g., graft or transplant rejections or allogenic reactions. Furthermore, soluble MAFA or anti-MAFA antibodies that stimulate (or block the inhibition of) NK and/or CTL function have therapeutic utility in the treatment of cancer or infectious diseases, particularly virus-mediated infectious diseases.

Definitions

To facilitate understanding the invention, and to provide additional guidance to one of skill in the practice of the invention, a number of terms are defined below. Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2d ed. 1994); The Cambridge Dictionary of Science and Technology (Walker ed., 1988); and Hale & Marham, The Harper Collins Dictionary of Biology (1991). Although any methods and materials similar or equivalent to those described herein can be used in the practice or testing of the present invention, preferred methods and materials are described. As used herein, the following terms have the meanings ascribed to them unless specified otherwise.

The term "antibody" refers to a peptide or polypeptide substantially encoded by an immunoglobulin gene or immunoglobulin genes, or fragments thereof, capable of specifically binding an epitope (e.g., from MAFA), see, e.g. Fundamental Immunology, Third Edition, W. E. Paul, ed., Raven Press, N.Y. (1993); Wilson (1994) J. Immunol. Methods 175:267–73; Yarmush (1992) J. Biochem. Biophys. Methods 25:85–97. One of skill will appreciate that antibody fragments may be isolated or synthesized de novo either chemically or by utilizing recombinant DNA methodology. The term antibody includes antigen-binding portions (e.g., fragments, subsequences) that retain capacity to bind antigen. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules; also known as single chain Fv (scFv); see e.g., Bird (1988) Science 242:423–426; Huston (1988) Proc. Natl. Acad. Sci. USA 85:5879–5883). Single chain antibodies are also included by reference in the term "antibody." Fragments can be prepared by recombinant techniques or enzymatic or chemical cleavage of intact antibodies. The term also includes multivalent antigen-binding proteins, see, e.g., U.S. Pat. No. 6,027,725. The term antibody also includes "chimeric" antibodies either produced by the modification of whole antibodies or those synthesized de novo using recombinant DNA methodologies. Such chimeric antibodies can be "humanized antibodies," i.e., where the epitope binding site is generated from an immunized mammal, such as a mouse, and the structural framework is human. Methods for making chimeric, e.g., "humanized," antibodies are well known in the art, see e.g., U.S. Pat. Nos. 5,811,522; 5,789,554; Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45. The term also includes human antibodies generated by transgenic non-human animals (e.g., mice) capable of producing human antibodies, as described by, e.g., U.S. Pat. Nos. 5,939,598; 5,877,397; 5,874,299; 5,814,318. The term antibody also includes epitope binding polypeptides generated using phage display libraries, and variations thereof, as described by, e.g., U.S. Pat. Nos. 5,855,885; 6,027,930.

As used herein, "isolated," when referring to a molecule or composition, such as, e.g., an agent that specifically binds to a MAFA on an NK or T cell or an agent that specifically binds to a MAFA ligand on a target cell, means that the molecule or composition is separated from at least one other compound, such as a protein, lipid, carbohydrate, DNA, RNA, or other contaminants with which it is associated in vivo or in its naturally occurring state. Thus, for example, an antibody is considered isolated when it has been isolated from any other component with which it is naturally associated or system in which it has been produced, e.g., by a hybridoma or by recombinant methods. An isolated composition, however, also can be substantially pure. An isolated composition can be in a homogeneous state. It can be in a dry or an aqueous solution. Purity and homogeneity can be determined, e.g., using any analytical chemistry technique, as described herein.

The term "mast cell function-associated antigen" or simply "MAFA" means any polypeptide that is functionally equivalent to the exemplary MAFA described herein, including human, mouse and rat MAFA polypeptides (SEQ ID NO:1, SEQ ID NO:3, or SEQ ID NO:5, respectively) or soluble MAFA-binding or MAFA ligand-binding fragments thereof, or equivalents thereof, and the nucleic acids encoding them (SEQ ID NO:2, SEQ ID NO:4, or SEQ ID NO:6, respectively). "Functional equivalency" means the polypeptide can specifically bind to a naturally occurring MAFA target cell or a MAFA target cell ligand. MAFA polypeptide equivalents falling within the scope of the invention can be determined by routine screening for their ability to specifically bind to a MAFA target cell or target cell ligand. Alternatively, MAFA polypeptides falling within the scope of the invention can be determined by routine screening for their ability as soluble polypeptide to block the interaction of an NK cell or T cell surface MAFA to interact with an MAFA target cell or a MAFA target cell ligand, as described herein. These MAFA polypeptides need not bind target cells or MAFA ligands with the same efficiency (e.g., affinity) as their wild type counterparts.

The pharmaceutical compositions of the invention also comprise "analogs," or "conservative variants" and "mimetics" ("peptidomimetics") of the exemplary polypeptides described herein, e.g., MAFA, anti-MAFA antibodies, MAFA ligand-binding polypeptides. Compositions within the scope of the invention comprise polypeptides with structures and activity that substantially correspond to the exemplary MAFA sequences, such as SEQ ID NO:1, SEQ ID NO:3 or SEQ ID NO:5, or soluble fragments thereof, or equivalents thereof. The pharmaceutical compositions of the invention also include "analogs," or "conservative variants" and "mimetics" ("peptidomimetics") of MAFA-binding (i.e., MAFA-recognizing) and MAFA ligand-binding compositions of the invention, e.g., anti-MAFA antibodies or MAFA-binding fragments thereof. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., the pharmaceutical composition agents comprising anti-MAFA antibodies or fragments thereof, MAFA binding or MAFA ligand-binding polypeptides. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature.

The term "pharmaceutical composition" refers to a composition suitable for pharmaceutical use in a subject. For example, the pharmaceutical compositions of this invention include formulations that comprise a pharmacologically effective amount of an agent that specifically binds to an MAFA ligand on a target cell. The pharmaceutical compositions of this invention also include formulations that comprise a pharmacologically effective amount of an agent that specifically binds to a cell surface MAFA on an NK or a T cell and a pharmaceutically acceptable carrier.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein or polypeptide") encoded completely or partially by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention. For example, the pharmaceutical compositions of the invention include recombinant MAFA binding or MAFA ligand-binding polypeptides and recombinant anti-MAFA antibodies or MAFA-binding fragments thereof, and the recombinant nucleic acids that encode them.

The term "specifically binding to" or "specifically recognizing" refers to antibody binding to a predetermined antigen. Typically, the antibody binds with an association constant (Ka) of at least about $1 \times 10^6$ M-1 or $10^7$ M-1, or about $10^8$ M-1 to $10^9$ M-1, or about $10^{10}$ M-1 to $10^{11}$ M-1 or higher, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" and "an antibody which binds specifically to an antigen" are used interchangeably.

Nucleic Acids

This invention provides pharmaceutical compositions comprising MAFA binding and MAFA ligand-binding polypeptides, e.g., soluble MAFA polypeptides, and anti-MAFA antibodies, and epitope binding fragments thereof, and the recombinant or isolated nucleic acids that encode them. Accordingly, the invention provides means to make and express those nucleic acids. As the genes and vectors of the invention can be made and expressed in vitro or in vivo, the invention provides for a variety of means of making and expressing these genes and vectors. One of skill will recognize that desired phenotypes associated with altered gene activity can be obtained by modulating the expression or activity of the genes and nucleic acids (e.g., promoters) within the vectors of the invention. The invention can be practiced in conjunction with any method or protocol known in the art, which are well described in the scientific and patent literature.

General Techniques

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including bacterial cells, mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence. Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The invention provides MAFA polypeptides and antibodies, and ligand/antigen binding subsequences/fragments of the polypeptides and antibodies. Use of amplification methods provides convenient techniques to generate modified, chimeric or truncated nucleic acid sequences that encode such polypeptides. Oligonucleotide primers can be designed to amplify nucleic acids encoding the desired MAFA or antibody polypeptides based on known MAFA sequences from human (SEQ ID NO:2), mouse (SEQ ID NO:4) or rat (SEQ ID NO:6) MAFA nucleic acid sequences (see below). Nucleic acids of the invention also can be, e.g., subcloned or measured quantitatively using amplification techniques. Amplification can also be used to identify nucleic acids in tissues or fluids or other samples.

The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152: 307–316; Sambrook; Ausubel; U.S. Pat. Nos. 4,683,195 and 4,683,202; Sooknanan (1995) Biotechnology 13:563–564. A continuous amplification reaction method is described by, e.g., U.S. Pat. No. 5,981,179.

Once amplified, the nucleic acids can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair.

The human MAFA polypeptide sequence is known in the art, e.g., GenBank Accession no. AAC34731 (see also Lamers (1998) Biochim. Biophys. Acta 1399,209–212):

```
  1 mtdsviysml elptatqaqn dygpqqksss skpscsclva itlglltavl lsvllyqwil (SEQ ID NO:1)
 61 cqgsnystca scpscpdrwm kygnhcyyfs veekdwnssl efclardshl lvitdnqems
121 llqvflseaf cwiglrnnsg wrwedgspln fsrissnsfv qtcgainkng lqasscevpl
181 hgvckkvrl
```

The human MAFA gene sequence, including the message (cDNA), is known in the art, e.g., GenBank Accession no. AF034952 (see also Lamers (1998) supra):

```
  1 atgactgaca gtgttattta ttccatgtta gagttgccta cggcaaccca agcccagaat (SEQ ID NO:2)
 61 gactacggac cacagcaaaa atcttcctct tccaagcctt cttgttcttg ccttgtggca
121 ataactttgg ggcttctgac tgcagttctt ctgagtgtgc tgctatacca gtggatcctg
181 tgccagggct ccaactactc cacttgtgcc agctgtccta gctgcccaga ccgctggatg
241 aaatatggta accattgtta ttatttctca gtggaggaaa aggactggaa ttctagtctg
301 gaattctgcc tagccagaga ctcacacctc cttgtgataa cggacaatca ggaaatgagc
361 ctgctccaag tttcctcag tgaggccttt tgctggattg gtctgaggaa caattctggc
421 tggaggtggg aagacggatc acctctaaac ttctcaagga tttcttctaa tagctttgtg
481 cagacatgcg gtgccatcaa caaaaatggt cttcaagcct caagctgtga agttccttta
541 cacgggtgt gtaagaaggt cagactttga
```

The mouse MAFA polypeptide sequence is known in the art, e.g., GenBank Accession no. CAA09342 (see also Blaser (1998) supra):

```
  1 madssiystl elpeapqvqd esrwklkavl hrphlsrfam valglltvil msllmyqril (SEQ ID NO:3)
 61 ccgskdstcs hcpscpilwt rngshcyyfs mekkdwnssl kfcadkgshl ltfpdnqgvk
121 lfgeylgqdf ywiglrnidg wrweggpals lriltnsliq rcgaihrngl qasscevalq
181 wickkvly
```

The mouse MAFA gene sequence, including the message (cDNA), is known in the art, e.g., GenBank Accession no. AJ010751 (see also Blaser (1998) supra):

```
  1 gtccctcatg gtgtttctca ccccacttac agcccacatt ccccactgag tgtgaaaggg (SEQ ID NO:4)
 61 atttggtaga gatggctgac agctctatct attcaacact agagctgccg gaggcacctc
121 aagtccaaga tgagtccaga tggaagctca aagctgtctt acaccggccc catctttccc
181 gctttgcaat ggtggctttg gggcttttga ctgtgattct catgagtcta ctgatgtatc
241 aacggatcct gtgctgcggc tccaaggact ctacatgttc ccactgcccc agctgcccca
301 tcctctgac gaggaatggt agccactgtt actatttttc aatggagaaa aaggactgga
361 attctagtct gaaattctgt gcagacaaag gctcacatct ccttacattt ccggacaacc
421 agggagtgaa gctgtttgga gagtacctgg gtcaggactt ttactggatc ggcttgagga
481 acattgatgg ctggaggtgg gaaggcggcc cagcgctcag cttgaggatt cttaccaaca
```

-continued

```
541 gcttgataca gaggtgcggt gccattcaca gaaatggcct ccaagcctcc agttgtgaag 601 ttgctttgca gtggatctgt aagaaggtcc tatactgatg gatgccactg tgtcctgagc 661 ctcggatctg ccacatgtgt ttaaaaagag ggaatgggtc tggggaatct ttgtctacaa 721 atgtgtgttt aacaaatgcc aaacctgtta tgatatgcca ttagacagag gattagcata 781 cctttctggg ggttggcctt ttcctgttgg gcttttccg cgactgttta agtattaggc 841 tagccattta aagcctaaat ctgggcaaat caaatgataa agcttattta atggataccc 901 accctgcaga tagccaccct ggctctctca tccttcctct gccatctctg tcaagagaga 961 gaaactatca tcctcagaga tgaccctgcg catcaga
```

The rat (Rattus norvegicus) MAFA polypeptide sequence is known in the art, e.g., GenBank Accession no. CAA56208 (see also Guthmann (1995) Proc. Natl. Acad. Sci. USA 92:9397–9401):

```
  1 madnsiystl elpaaprvqd dsrwkvkavl hrpcvsylvm valglltvil mslllyqrtl  (SEQ ID NO:5)

61 ccgskgfmcs qcsrcpnlwm rngshcyyfs mekrdwnssl kfcadkgshl ltfpdnqgvn 121 lfqeyvgedf ywiglrdidg wrwedgpals lsilsnsvvq kcgtihrcgl hasscevalq 181 wicekvlp
```

The rat MAFA gene sequence, including the message (cDNA), is known in the art, e.g., GenBank Accession no. X79812 (see also Guthmann (1995) supra):

```
   1 caccctgctt actgtcgtca ctccctgctg agtgtgaagg gcgttgggtg gagatggccg  (SEQ ID NO:6)

61 acaactctat ctactcaaoa ttagagctgc ctgctgcacc tcgagtccaa gatgactcca 121 gatggaaggt caaagctgtc ttacaccgac cctgtgtttc ctaccttgtg atggtggctt 181 tggggctttt gactgtgatt ctcatgagtc tactgttgta ccaacggact ctgtgctgtg 241 gctccaaggg ctttatgtgt tcccagtgct ccaggtgccc caacctctgg atgaggaacg 301 ggagcoactg ttactacttc tcaatggaga aagggactg gaactctagt ctgaagttct 361 gtgcagacaa aggctcgcat ctccttacat ttccggacaa ccagggagtg aacctgttcc 421 aggagtatgt gggcgaggac ttttactgga ttggcttgag ggacatcgat ggctggaggt 481 gggaagatgg cccagctctc agcttaagca ttctctctaa cagcgtggta cagaagtgtg 541 gcaccatcca caggtgtggc ctccacgcct ccagttgtga ggttgctttg cagtggatct 601 gtgagaaggt cctgccctga aggattccac tgtgtcccaa gcctcagatc tgccacatgt 661 cttcaaaaag agggaatggg catggggaac ctctgttcac aaaggtgtct ttagcaaatg 721 ccaaacotgt tatgatatgc cattagacag gcgttagcat tccttcctgg gagctggcat 781 ttttcaactg ggctttctca gtcatgttag ccatttaaag cctaaatctg gcaaatgaa 841 atagataaaa tttattttga tggctcttac tgcacaaact caccctggct ttctcatccc 901 atactctgcc atatctatca aagatatgtg caaaactatt catctgcaga gaaccccca 961 ccacggtcaa taacacatta catagacatc gaatagagac agaaaagcaa acacctcctg 1021 ttctcactcc tgcttggaag ctgaagtagc tcaagcctga ggtgcaggga gaagtgcagt
```

```
                                                    -continued
1081  ggttaccaga gtccaggaga ctgaagggat ggtagaggtt ggttaatggt ttggctggtg 1141  tggggtgacc atcatgatta atgattgttg tatgtttgcc aatatgttgt gaacttccgg 1201  atagcgaggt ggaaggaccg tgggtgttac caaatgcctg caggagagat gtgctgagaa 1261  ccctgactgg atgatttcca cacacattga aatatcacac tgtgccccat aaatgtgtac 1321  aatcattatc tatccctaat ttccctaaaa attaaagaag tcccaattaa aataaaaaat 1381  acctttctgc taaaaaaaaa aaaaaaaaaa aaaaaaaaaa aaaaaaaaaa aaaaaaaaaa 1441  aaaaaaaaaa aaaaaaaaa a
```

Polypeptides

The invention provides MAFA polypeptides (e.g., SEQ ID NO:1, SEQ ID NO:3, SEQ ID NO:5) and subsequences of thereof, e.g., soluble ligand-binding MAFA fragments. These MAFA polypeptides can be used in the pharmaceutical compositions and methods of the invention; they can also be used as immunogens to generate antibodies capable of blocking the binding of cell surface expressed MAFA to its target cell ligand or to bind to MAFA and stimulate or initiate its activity ("agonist activity") or decrease or block its activity ("antagonist activity"). These polypeptides and peptides can also be used to identify the presence of human antibodies that specifically bind to them. Polypeptides of the invention also include anti-MAFA antibodies, as described herein.

Polypeptides and peptides of the invention can be isolated from natural sources, they can be synthetic, or they can be recombinantly generated polypeptides. Peptides and proteins can be recombinantly expressed in vitro or in vivo. The peptides and polypeptides of the invention can be made and isolated using any method known in the art, and the invention provides a few exemplary means for generating such proteins.

Polypeptide and peptides of the invention can be synthesized, whole or in part, using chemical methods well known in the art. See e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified peptides of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896.

Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and GCA-associated peptide or polypeptide can be useful to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–14). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Anti-MAFA Antibodies

The pharmaceutical compositions of the invention include anti-MAFA antibodies, and epitope/antigen binding fragments thereof, and the recombinant or isolated nucleic acids that encode them. These antibodies can be used to manipulate NK and T cell activities, as described herein, or, alternatively, these antibodies can be used in the isolation, detection or quantitation of the soluble MAFA polypeptides or peptides of the invention.

Methods of producing polyclonal and monoclonal antibodies are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Such techniques include antibodies from libraries of recombinant antibodies displayed in phage ("phage display libraries") or on cells; or humanized antibodies, or human antibodies made in non-human animals (see definition of "antibody", above). Recombinant antibodies can be expressed by transient or stable expression vectors in mammalian cells, as in Norderhaug (1997) J. Immunol. Methods 204:77–87; Boder (1997) Nat. Biotechnol. 15:553–557.

Such techniques include selection of MAFA-reactive antibodies from libraries of recombinant antibodies displayed on phage ("phage display libraries") or on cells. See, e.g., Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45. Recombinant antibodies can also be expressed by transient or stable expression vectors in mammalian cells, as in Norderhaug (1997) J. Immunol. Methods 204:77–87; Boder (1997) Nat. Biotechnol. 15:553–557. Specific monoclonal and polyclonal antibodies and antisera can bind with a KD of at least about 1 µM, or about 0.1 µM or about 0.01 µM or better.

In one embodiment, the peptides are used as immunogenic compositions to generate an anti-MAFA response in a non-human animal. The peptide can be conjugated to another molecule or can be administered with an adjuvant. Alternatively, DNA encoding a polypeptide comprising a MAFA epitope of the invention can be administered to generate an immune response. The coding sequence is part of an expression cassette or vector capable of expressing the immunogen in vivo. (see, e.g., Katsumi (1994) Hum. Gene Ther. 5:1335–9).

Pharmaceutical Compositions

The invention provides pharmaceutical compositions comprising an agent that specifically binds to an MAFA ligand on a target cell and pharmaceutical compositions comprising an agent that specifically binds to an NK- or a T cell-expressed cell surface MAFA, and a pharmaceutically acceptable excipient. In alternative embodiments, the agents comprise MAFA polypeptides and soluble ligand binding fragments thereof, and anti-MAFA antibodies and antigen binding fragments thereof. The polypeptide-containing pharmaceuticals of the invention can be administered to, e.g., arrest the progress, reduce the severity, or prevent the recurrence of ("ameliorate") autoimmune disease or graft or organ rejection or an allogenic response, increase NK cell or T killer cell (CTL) activity, increase NK cell or CTL activity against virally infected cells or tumor cells, effect cytokine secretion by NK cells or T cells, and the like.

Formulation and Administration of Peptide Pharmaceutical Compositions

Pharmaceutically acceptable carriers and formulations for polypeptides are known to the skilled artisan and are described in detail in the scientific and patent literature, see e.g., the latest edition of Remington's Pharmaceutical Science, Maack Publishing Company, Easton, Pa. ("Remington's"); Banga; Putney (1998) Nat. Biotechnol. 16:153–157; Patton (1998) Biotechniques 16:141–143; Edwards (1997) Science 276: 1868–1871; Ho, et al., U.S. Pat. No. 5,780,431; Webb, et al., U.S. Pat. No. 5,770,700; Goulmy, et. al., U.S. Pat. No. 5,770,201.

The polypeptide-containing pharmaceutical compositions used in the methods of the invention can be delivered alone or as pharmaceutical compositions by any means known in the art, e.g., systemically, regionally, or locally; by intraarterial, intrathecal (IT), intravenous (IV), parenteral, intrapleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method of administration. Dosages for polypeptide-containing pharmaceutical compositions are well known to those of skill in the art. Such dosages are typically advisorial in nature and are adjusted depending on a variety of factors, e.g., the initial response (e.g., stimulation or inhibition of an NK or a T cell activity), the particular therapeutic context, patient health and tolerance. The amount of polypeptide-containing pharmaceutical adequate to generate the desired response (e.g., effect on the immune system, NK cells or T cells) is defined as a "therapeutically effective dose." The dosage schedule and amounts effective for desired uses, i.e., the "dosing regimen," will depend upon a variety of factors, including the stage of the tumors (e.g., when stimulating NK or T cell killing of tumor cells), the severity of the disease or condition (e.g., when inhibiting an autoimmune response mediated by an NK or a T cell), the general state of the patient's health, the patient's physical status, age, pharmaceutical formulation and concentration of excipient, and the like. The dosage regimen also takes into consideration pharmacokinetics, i.e., the polypeptide-containing pharmaceutical composition's rate of absorption, bioavailability, metabolism, clearance, and the like, see, e.g., Remington.

Dosages can be determined empirically, by assessing the abatement or amelioration of symptoms, or by objective criteria, such analysis of blood or histopathology (e.g., tumor) specimens. Successful treatment can also be monitored by histopathology.

The pharmaceutical compositions of the invention can be administered alone or in conjunction with other therapeutic treatments. As noted above, a single or multiple administrations (immunizations) of the compositions may be administered depending on the dosage and frequency as required and tolerated by the patient. Dosages also can be determined empirically, by assessing the abatement or amelioration of symptoms, or by objective criteria, such analysis of blood or histopathology specimens.

The pharmaceutical compositions containing the peptide and complexes of the invention can be administered alone or in conjunction with other therapeutic treatments. Single or multiple administrations of the compositions may be administered depending on the dosage and frequency as required and tolerated by the patient.

Kits

The invention provides kits that contain the pharmaceutical compositions of the invention. Kits containing pharmaceutical preparations can also include printed matter, e.g., directions as to indications, dosages, routes and methods of administration, and the like.

EXAMPLES

The following examples are offered to illustrate, but not to limit the claimed invention.

Example 1

Anti-MAFA Antibodies and Soluble MAFA can be Used to Manipulate NK Cell and T Cell Activities The following example demonstrates that treatment of NK cells or cytotoxic T cells (CTL) expressing MAFA with anti-MAFA antibodies inhibited the cytotoxic activity of both cells. The example also demonstrates that soluble, recombinant MAFA augmented NK cell cytotoxic activity.

Recombinant soluble murine MAFA (rsMAFA) was prepared. Rat monoclonal antibodies against murine rsMAFA were generated and shown to bind to cell surface MAFA. Treatment of mouse NK cells or CTL expressing MAFA with these antibodies inhibited the cytotoxic activity of both cells. Soluble MAFA augmented NK cell cytotoxic activity. These results demonstrated that MAFA functions to regulate the cytotoxic functions of NK cells and CTL. Thus, these results also demonstrate that the compositions and methods of the invention, by manipulating MAFA-associated cellular activities, can be used to regulate functions of NK cells and T cells.

Materials and Methods

Animals: Fisher and S.D. rats were purchased from Harlan (Indianapolis, Ind.). C3H/HeJ mice were purchased from The Jackson Laboratory (Bar Harbor, Mass.).

Antibodies and cells: Anti-HA antibody, anti-His antibody, and anti-His agarose were purchased from Babco. Anti-FLAG (M2) antibody and anti-FLAG agarose were purchased from SIGMA (St Louis, Mo.). Anti-DX5 antibody-PE conjugated and anti-CD16/CD32 antibody were purchased from Pharmingen. Anti-rat IgG antibody-PE conjugated was purchased from Southern Biotechnology Associates, Inc. HEK293 cells and RBL cells were a gift from Dr. Carl Ware and Dr. Yun-Cai Liu, respectively. 3Y1 cells were obtained from RIKEN (Tokyo). VSV peptide-specific mouse CTL lines were generated as previously described by Franco (1999) J. Immunol. 162:3388–3394.

cDNA cloning of mouse MAFA: Mouse spleen QUICK-Clone cDNA (CLONTECH) was used as a template, and PCR was performed to amplify mouse MAFA cDNA fragment with primers (5'-CCTTGTGATGGTG-GCTTTGGGGCTTTTGACTG-3' (SEQ ID NO:7) and 5'-ACTGCAAAGCAACCTCACAACTGGAGGC-3') (SEQ ID NO:8) from the rat MAFA DNA sequence (SEQ ID NO:6) at 95° C. for 5 sec, 55° C. for 30 sec and 72° C. for 2 min for 30 cycles. The amplified cDNA fragment was labeled with 32P using the Prime-It II random primer labeling kit (Stratagene, San Diego, Calif.) and used as a probe for screening a mouse spleen cDNA library (Stratagene) using plaque hybridization, as described by Sambrook. One clone, containing a nearly full-length cDNA encoding murine MAFA, with the exception of four amino acids at the N-terminus, was obtained.

Expression and production of MAFA protein: To express FLAG-tagged MAFA, a cDNA encoding amino acid residues 64 to 188 of the extracellular domain of mouse MAFA was amplified by PCR using the cloned mouse MAFA cDNA as a template with primers (5'-ATATGGATCCTCCAAG-GACTCTACATGTTC-3' (SEQ ID NO:9) and 5'-ATAT-GCGGCCGCTCAGTATAGGACCTTCTTACAG-3' (SEQ ID NO:10) and inserted into pFastBac donor plasmids (Gibco BRL) at the 3'-end of a honey bee melittin signal peptide and FLAG tag. To express His-tagged MAFA, a cDNA fragment was amplified by PCR with primers (5'-CCC GGA TCC GCA TCA CCA TCA CCA TCA CGC GGC CGC TTC CAA GGA CTC TAC ATG TTC CCA CTG C-3' (SEQ ID NO:11) and 5'-ATA TGC GGC CGC TCA GTA TAG GAC CTT CTT ACA G-3') (SEQ ID NO:12) and inserted into pFastBac donor plasmids (Gibco BRL) at 3'-end of a honey bee melittin signal peptide.

Recombinant baculoviruses carrying the MAFA gene were generated according to the manufacturer's instructions. Tn5 insect cells were infected with the viruses and cultured for 4 days. The supernatant was mixed with M2-agarose (SIGMA) for FLAG-tagged MAFA or with Mono 6-His Affinity Matrix (Babco) for His-tagged MAFA. After overnight incubation at 4 oC, the agarose was packed in a column and washed with 10 vol. of 20 mM Tris-HCl (pH 7.5) containing 0.5M MgCl2, and 0.5% NP-40. The MAFA protein was eluted with 20 mM Glycine-HCl (pH 3.0). Endotoxin in the preparation was measured using PYRO-TELL (CAPE COD). For cell surface expression of myc-tagged mouse MAFA, a full-length cDNA of MAFA gene was amplified by PCR using the cloned cDNA with primers (5'-CCCAAGCTTACAACCA TGGCTGACCGCTC-TATCGCCTCAACAGCCGAGCTGCCGGAG-GCACCTCAAGTCCAA G-3' (SEQ ID NO:13) and 5'-CCCCTCGAGCTACAGATCCTCTTCA-GAGATGAGTTT CTGCTCGTATAGGACCTTCTTACA-GATCCA-3') (SEQ ID NO:14) and inserted into the expression vector pCDNA3.1/Hygro (Invitrogen), and transfected into HEK293 cells. Stable transfectants were selected with 50 ug/ml Hygromycin B. For cell surface expression of HA-tagged mouse MAFA, a full-length cDNA of the mouse MAFA gene was amplified by PCR with primers (5'-CGA-CAACTCTATCTACTCAACACTAGAGCTGC-3' (SEQ ID NO:15) and 5'-CACAGAATTTCAGACTCGAGTTC-CAGTCCTT-3' (SEQ ID NO:16), or 5'-ACTGGAACT CGAGTCTGAAATTCTGTGCAG-3' (SEQ ID NO:17) and 5'-GGATGAATTCCCCGTATAG GACCTTCTTACAG-3') (SEQ ID NO:18), followed by the digestion of XhoI, ligation of the cDNA fragments, and PCR amplified again with primers (5'-ACGAATTCACAACCAT GGCCGA-CAACTCTATCTAC-3' (SEQ ID NO:19) and 5'-GGAT-GAATTCCCCGTATA GGACCTTCTTACAG-3') (SEQ ID NO:20). The cDNA fragment was inserted into a pEF-neo vector and transfected into RBL cells and 3Y1 cells. Stable transfectants were selected with 0.4 mg/ml G418.

Production of monoclonal antibodies: Two S.D. and two fisher rats were immunized i.p. with 100 ug of FLAG-tagged MAFA protein in CFA. After 3 weeks, 100 ug of His-tagged MAFA in 'IFA was used to boost the animals i.p. 3 weeks later, the animals were boosted i.p. again with 100 ug of FLAG-tagged MAFA in IFA. Finally, 5 X 106 3Y1 cells expressing HA-tagged MAFA were used to immunize the mice i.p. without adjuvant. After 3 days, the spleens were harvested and the spleen cells were fused with the myeloma cell line (SP2/O-Ag14) (17). Hybridomas were screened by staining of the transfectants. For IgG purification, hybridomas were cultured in CELLine (IBS) and antibody was purified using a protein G affinity resin. Biotinylation of the antibodies was performed by using a biotin labeling kit (Boehringer Mannheim). F(ab')2 antibody was produced by ImmunoPure F(ab')2 preparation kit (PIERCE).

NK cell assay: Poly I:C or mouse IL-2 was used for the activation of NK cells. 100 ug Poly I:C was injected i.p. into mice. After three days, spleen cells were prepared and used in the NK cell assay. Alternatively, mouse spleen cells were cultured with 20 ng/ml of mouse IL-2 for four days. 51Cr release cytolytic assays were performed as previously described by Sentman (1988) Nat. Immun. Cell Growth Regul. 7:95. Antibodies and soluble MAFA were added when the target cells were mixed with the NK cells.

CTL assays: Culturing of CTL, and CTL cytolytic assay were performed as described by Franco (1999) supra.

Results

Isolation of Monoclonal Anti-mouse MAFA Antibodies

Recombinant soluble murine MAFA (rsMAFA) was expressed in Tn5 insect cells. A honey bee melittin signal peptide was found to allow for efficient secretion of the MAFA protein from the cells, while a human VCAM signal peptide generally used for expression of type II receptors (see, e.g., Crowe (1994) Science 264:707–10) failed to efficiently allow for secretion. Approximately 0.5 mg of rsMAFA was expressed and secreted into 1 L culture supernatant. After purification, it was confirmed that the murine rsMAFA was able to bind to fungi-derived proteins such as *Aspergillus oryzae* amylase or yeast carboxy peptidase Y, which indicated that the soluble MAFA retained its lectin function. The rsMAFA protein tagged by FLAG or His peptide was used to reciprocally immunize rats in order to prevent antibody formation to the tagged peptide. MAFA-expressing transfected cells were also used to immunize at the final boosting stage in order to enhance the antibody response to cell surface MAFA.

Among 600 hybridomas screened, two clones producing anti-MAFA antibody were selected, 1F10 and 7B5. These antibodies stained myc-tagged MAFA expressing transfectants. Myc-tagged MAFA transfected and non-transfected HEK239 cells were stained with (A) 10 ug/ml 9E10, anti-myc antibody, (B) 10 ug/ml 1F10, (C) 1 ug/ml 1F10, (D) 0.1 ug/ml 1F10, (E) 10 ug/ml 7B5, (F) 1 ug/ml 7B5, (G) 0.1 ug/ml 7B5. After incubation of 1st antibody, goat F(ab')2 anti-rat IgG PE conjugated was used as 2nd antibody for anti-mouse MAFA monoclonal antibodies, and goat F(ab')2 anti-mouse IgG PE conjugated was used as 2nd antibody for 9E10.

One of the two antibodies, 1F10, did not stain a DX5+ population from non-stimulated mouse spleen cells. Mouse IL-2 stimulated and non-stimulated spleen cells were stained with anti-MAFA antibody 1F10-biotin/SA-APC, and anti-mouse DX5 antibody-PE conjugated. Since DX5 is a known NK cell marker this result suggests that non-stimulated NK cells do not express MAFA. In IL-2 activated splenocytes, the population of DX5+ cells was increased from 10% in non-stimulated splenocytes to about 50% in activated splenocytes. Interestingly, the proportion of MAFA+ cells in the DX5+ population was increased to 10% after activation of the NK cells.

Figure 1B:
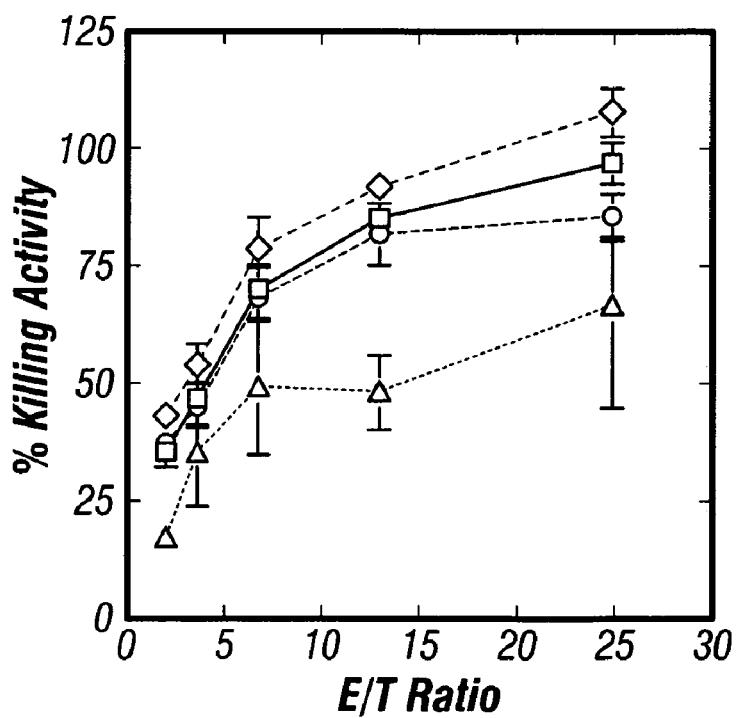
Figure 2A:
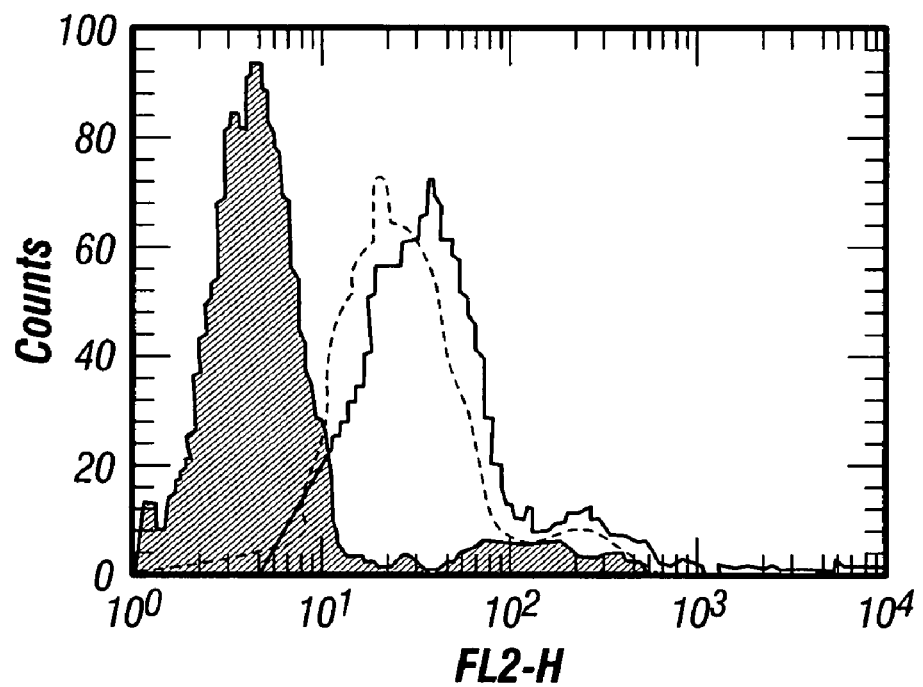
FIG. 2 shows staining activities as measured by FACS analyzer demonstrating that soluble recombinant MAFA stained the NK target cells YAC-1 and EL-4, as described in detail in Example 1. 10 ug/ml (FIG. 2A, FIG. 2D), 1 ug/ml (FIG. 2B, FIG. 2E), 0.1 ug/ml (FIG. 2C, FIG. 2F) of soluble MAFA protein were incubated with YAC-1 (FIG. 2A, FIG. 2B, FIG. 2C) and EL-4 (FIG. 2D, FIG. 2E, FIG. 2F).
Figure 2B:
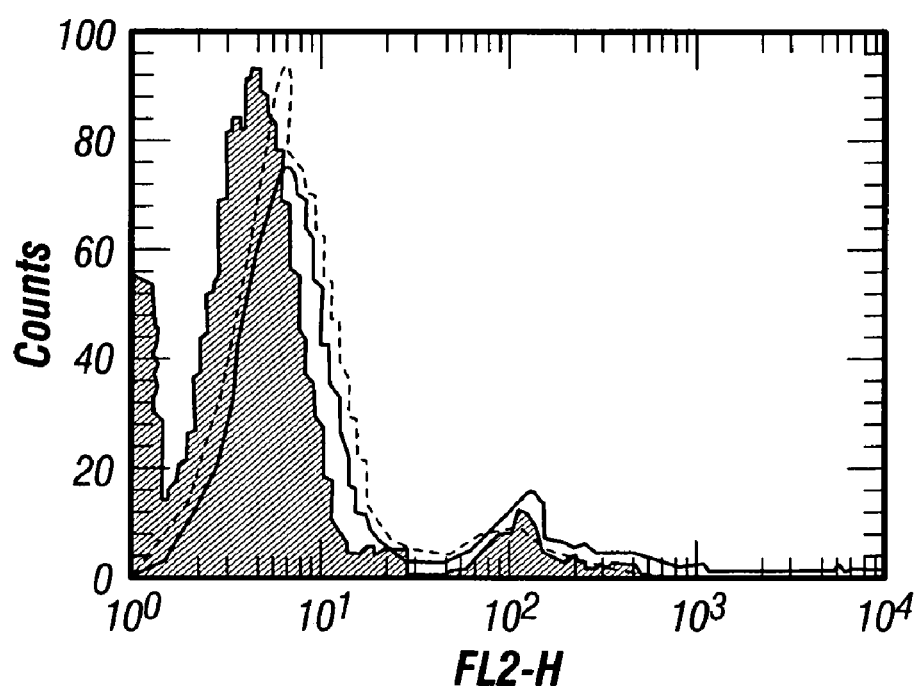
Figure 2C:
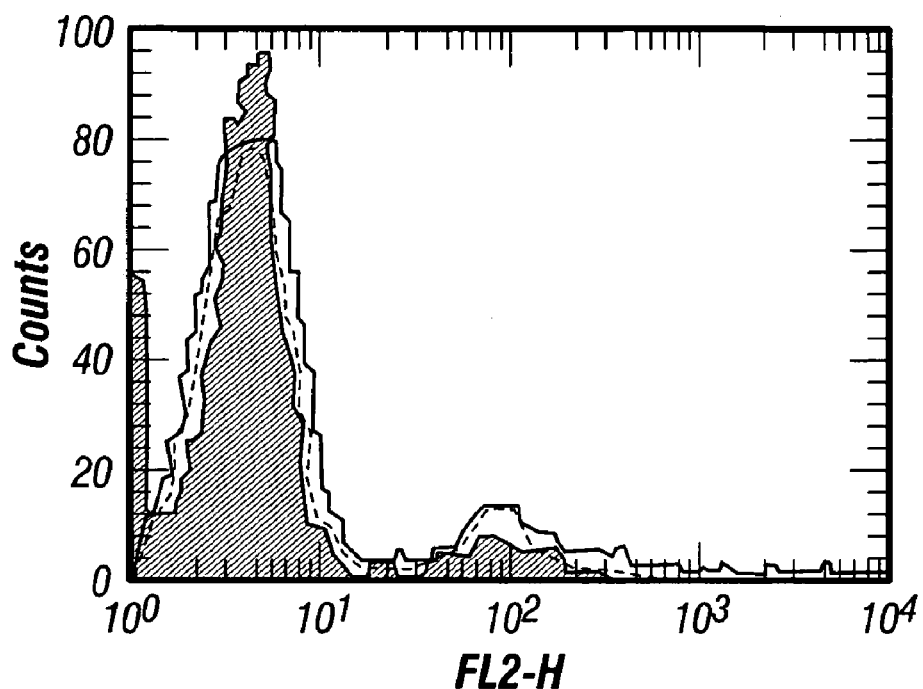
Figure 2D:
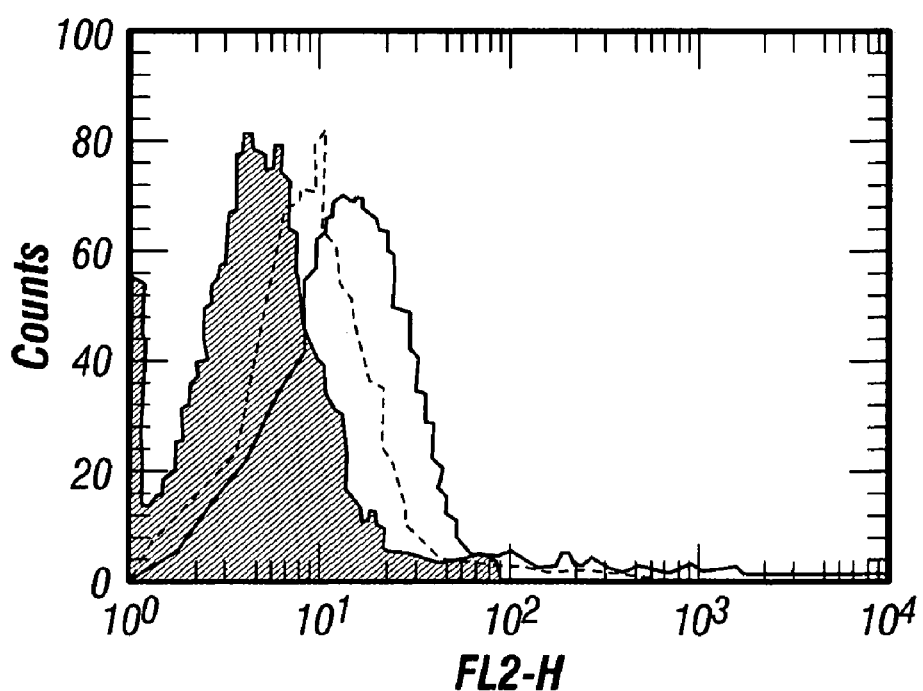
Figure 2E:
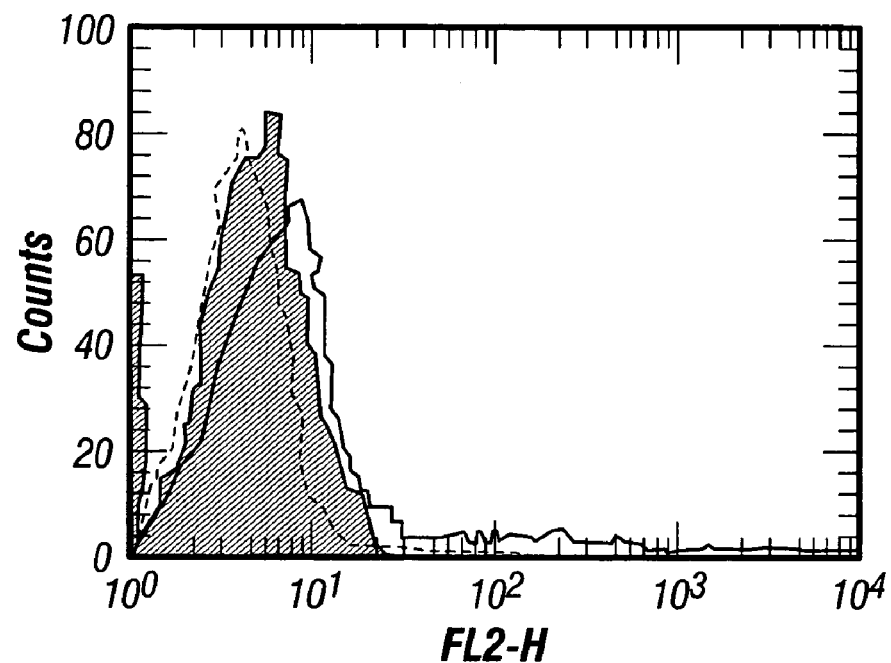
Figure 2F:
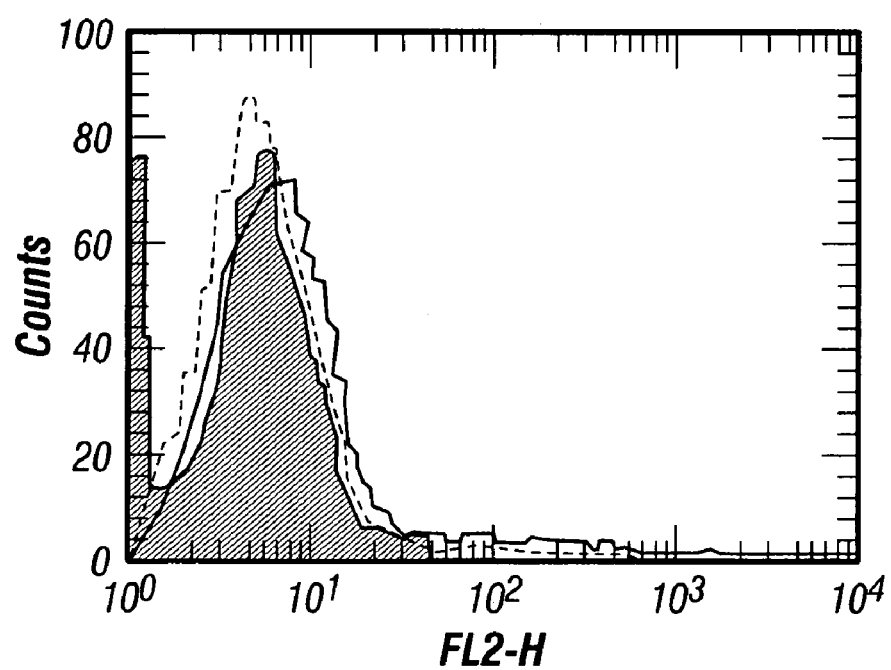

Inhibition of the Cytotoxic Activity of NK Cells by Monoclonal Anti-MAFA Antibodies The activity of anti-MAFA antibodies on NK cell function was investigated. To exclude the possibility of an ADCC (antibody dependent cell mediated cytotoxicity) reaction, F(ab')2 fragments of the two antibodies were prepared and added to activated NK cell fractions. The binding ability of the F(ab')2 fragments to MAFA expressed on the cell surface was not changed. FIG. 1 summarizes the data showing the effect of anti-mouse MAFA antibodies on NK cytolytic assays against YAC cells. Concentrations of 5 ug/ml (FIG. 1A), and 0.5 ug/ml (FIG. 1B) F(ab')2, were used with PBS (square), F(ab')2 from normal rat IgG (lozenge), 1F10 (circle), 7B5 (triangle). Horizontal bar represents the ratio of effector (mouse IL-2 activated spleen cells) and target (YAC-1).

As shown in FIG. 1, the F(ab')2 fragments of 7B5 (triangle) and 1F10 (circle) inhibited approximately 95% and 70%, respectively, of the cytotoxic activity of the NK cells against YAC-1 cells at a concentration of 5 ug/ml (FIG. 1A), whereas F(ab')2 fragments from normal rat IgG (lozenge) failed to inhibit the activity of NK cells. These results indicate that MAFA plays an important role in the regulation of the cytotoxic function of NK cells and that the pharmaceutical compositions and methods of the invention can be used to inhibit that activity.

Enhancement of the Cytotoxic Activity of NK Cell by Recombinant Soluble MAFA

If the cytotoxic activity of NK cells is regulated through MAFA and its interaction with its ligand, target cells killed by NK cells should express MAFA ligand. Indeed, typical NK target cells, YAC-1 and EL-4 cells, demonstrated staining with soluble MAFA, as shown in FIG. 2. Soluble recombinant MAFA bound to surface molecule(s) expressed by the target cells. EGTA treatment reduced soluble MAFA binding, indicating that binding was Ca2+ dependent. This is common in the interaction of lectin type receptors with their ligands.

FIG. 2 shows a FACS cell staining histogram of NK targets cells. YAC-1 cells and EL-4 cells were stained with soluble, recombinant mouse MAFA protein. 10 ug/ml (FIG. 2A, FIG. 2D), 1 ug/ml (FIG. 2B, FIG. 2E), 0.1 ug/ml (FIG. 2C, FIG. 2F) of soluble MAFA protein were incubated with YAC-1 (FIG. 2A, FIG. 2B, FIG. 2C) and EL-4 (FIG. 2D, FIG. 2E, FIG. 2F), and followed by the incubation with anti-FLAG antibody, and Goat F(ab')2 anti-mouse IgG PE conjugated. Filled curve represent no soluble MAFA, gray lines represent soluble MAFA, and dot lines represent soluble MAFA and 1 mM EGTA. Staining activities were measured by FACS analyzer.

Figure 3:
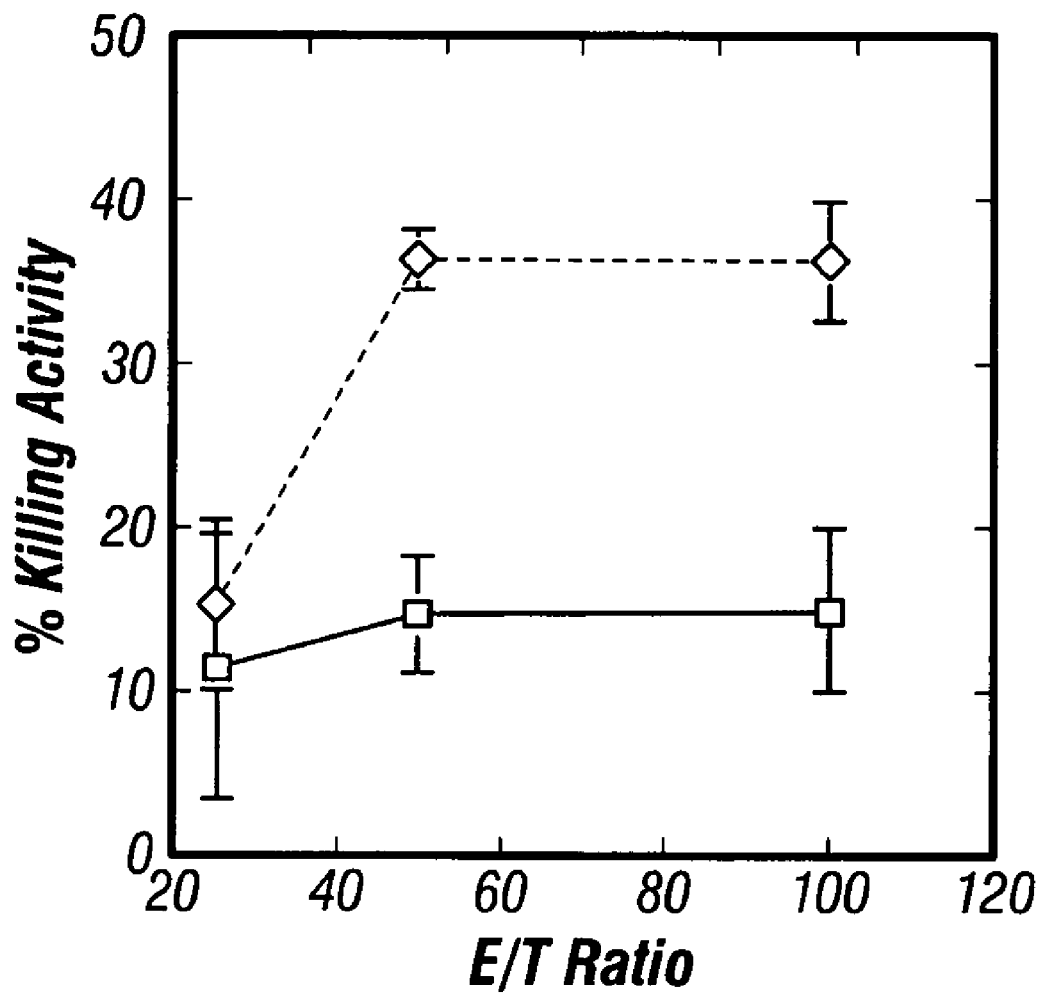
FIG. 3 is a graph summarizing data showing the effect of 10 ug/ml of soluble, recombinant MAFA on the cytotoxic activity of NK cells against YAC-1 cells, as described in detail in Example 1.
Figure 4A:
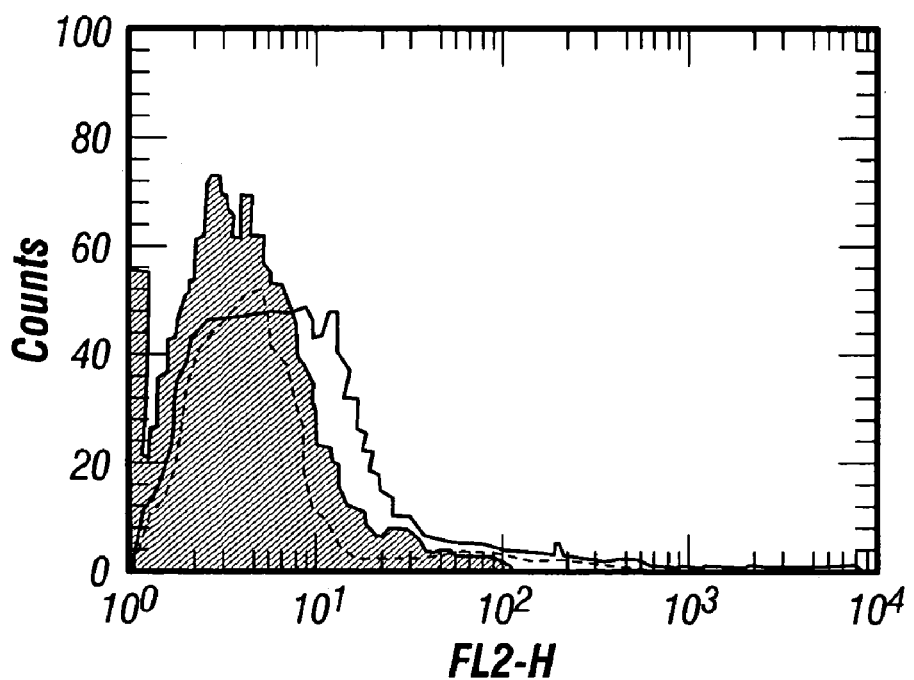
FIG. 4 shows staining activities as measured by FACS analyzer demonstrating that anti-MAFA antibodies stained CTLs, as described in detail in Example 1. Two lines of CTLs, line 1 (FIG. 4A, FIG. 4C) and line 2 (FIG. 4B, FIG. 4D) were tested with 1F10 (FIG. 4A, FIG. 4B) and 7B5 (FIG. 4C, FIG. 4D).
Figure 4B:
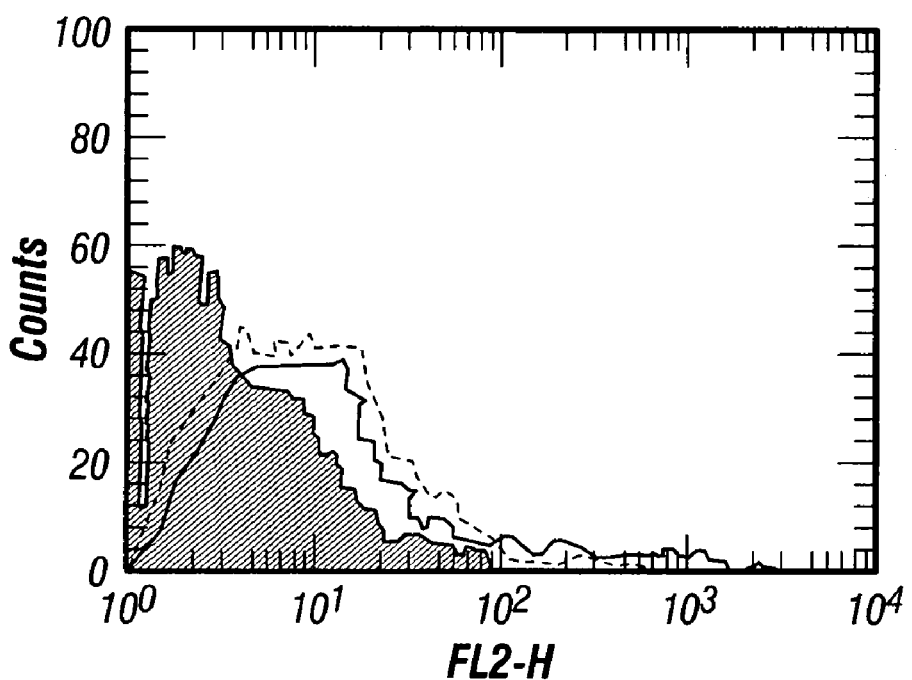
Figure 4C:
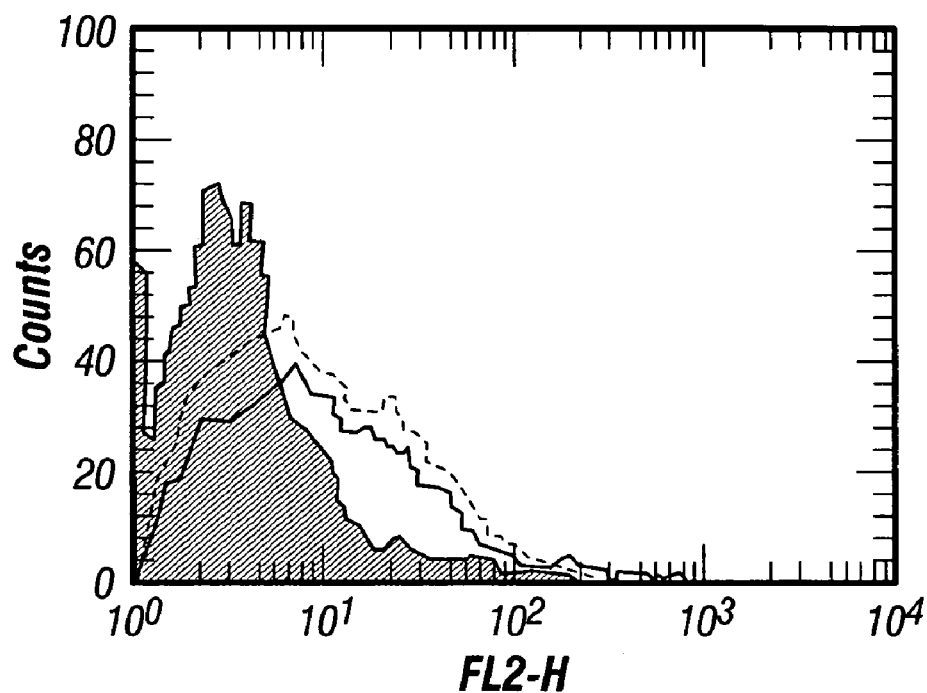
Figure 4D:
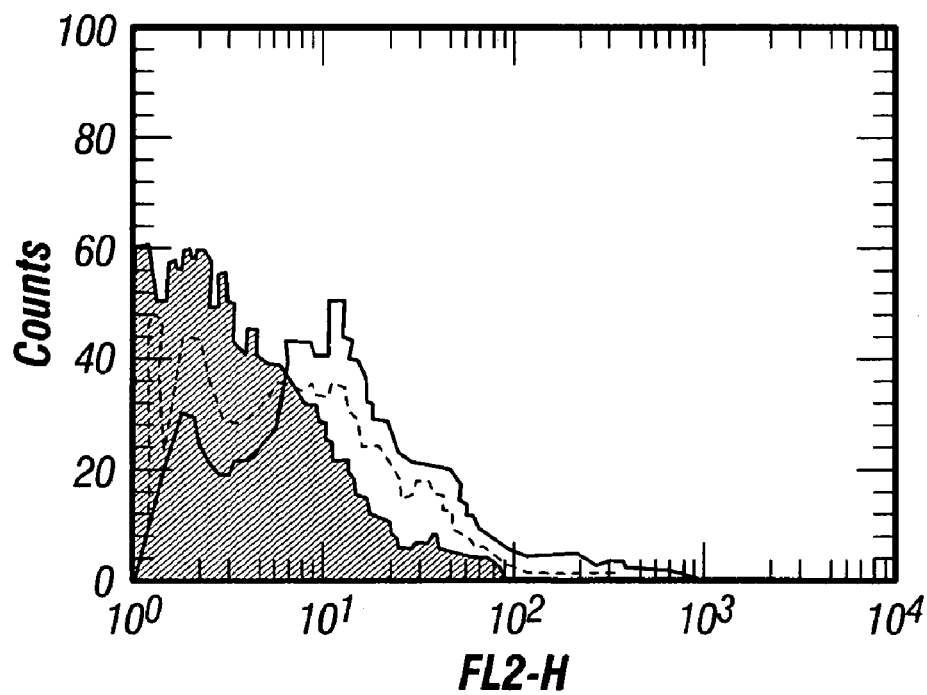

Next, the activity of soluble, recombinant MAFA was examined. It was determined that its binding to NK target cells negatively regulates the cytotoxic activity of NK cells. The killing activity of ploy I:C activated NK cells were measured in the presence (lozenge) or absence (square) of 10 ug/ml of soluble MAFA. Horizontal bar represents the ratio of effector (mouse IL-2 activated spleen cells) and target (YAC-1). As shown in FIG. 3, 10 ug/ml of soluble, recombinant MAFA enhanced the cytotoxic activity of NK cells against YAC-1 cells. This result demonstrate that MAFA expressed by NK cells, like other ITIM motif-containing NK receptors, plays a negative regulatory role in their cytotoxic function, and that the pharmaceutical compositions and the methods of the invention can be used to manipulate that function.

Inhibition of the Cytotoxic Activity of CTL by Monoclonal Anti-MAFA Antibodies

The ability of soluble, recombinant MAFA to stain CTLs (activated by VSV peptides) was demonstrated, as shown in FACS histogram cell staining profiles depicted in FIG. 4. The staining activities of anti-MAFA antibodies on CTLs were measured. Two lines of CTLs, line 1 (FIG. 4A, FIG. 4C) and line 2 (FIG. 4B, FIG. 4D) were tested with 1F10 (FIG. 4A, FIG. 4B) and 7B5 (FIG. 4C, FIG. 4D). Filled curve represent control staining; gray curve represent anti-MAFA antibody staining.

Figure 5:
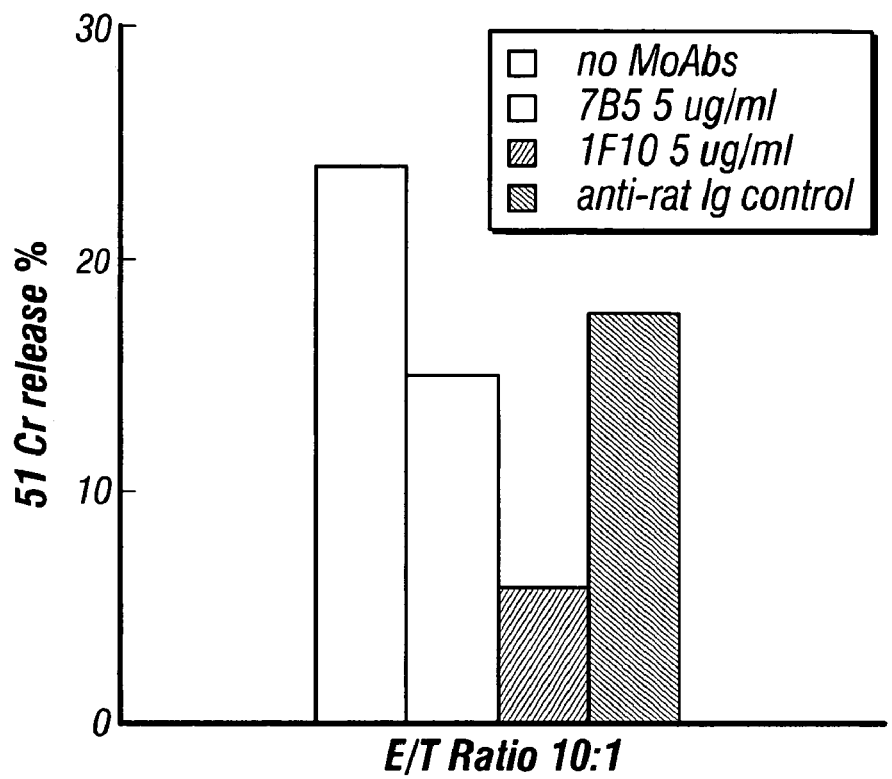
FIG. 5 shows data summarizing the modulation of CTL cytolytic activity against EL-4 cells by anti-MAFA antibodies, as described in detail in Example 1.
Figure 5:
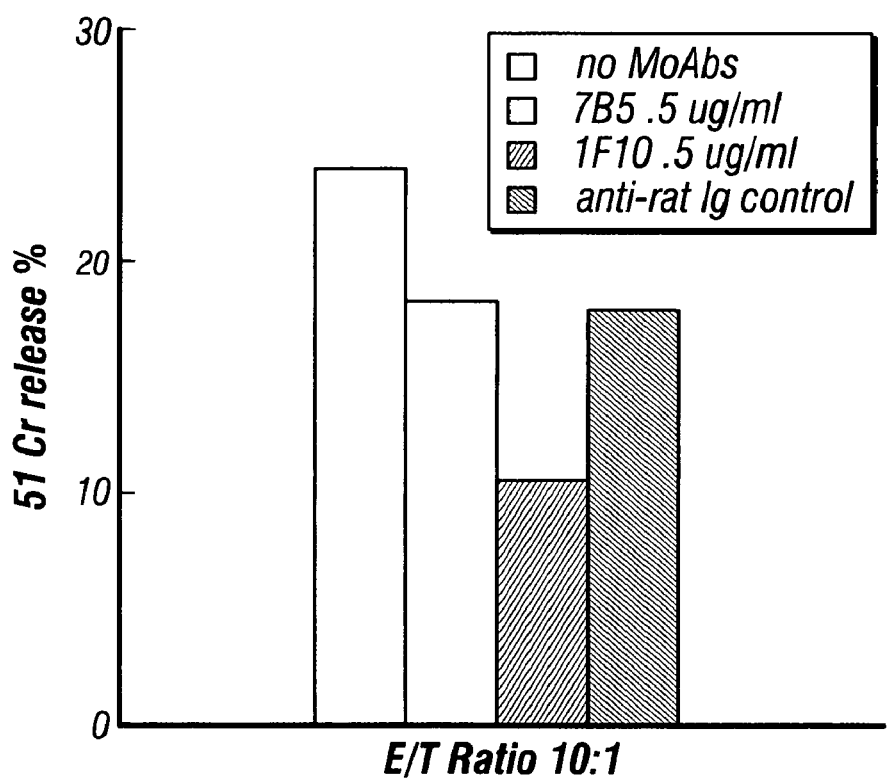

The modulation of CTL cytolytic activity against EL-4 cells by anti-MAFA antibodies was demonstrated, as shown in FIG. 5. CTLs (activated with VSV peptides) were investigated in the absence of antibody, (1st column from left), or in the presence of 7B5 (2nd column), 1F10 (3rd column), and normal rat IgG (4th column). FIG. 5A (upper panel) shows the result when the anti-MAFA antibodies were used at a concentration of 5 ug/ml, while FIG. 5B (lower panel) shows the result when the anti-MAFA antibodies were used at a concentration of 0.5 ug/ml. In the presence of anti-MAFA antibody, the cytolytic activity of these cells against EL-4 target cells was substantially suppressed.

In summary, to examine the function of MAFA, recombinant soluble murine MAFA and monoclonal antibodies to mouse MAFA were generated. Cell staining analyses using the antibodies revealed that the expression of MAFA on the NK cell surface is regulated by the activation state of the cells. In contrast to NK cells, peptide-specific CTL clones established from peptide-specific TCR transgenic mice failed to react with anti-MAFA antibodies. However, in vivo primed peptide-specific CTL were stained by the anti-MAFA antibodies. These results are inconsistent with a previous finding (Blaser (1998) supra) that MAFA expression was induced only in vivo by priming with live virus. Furthermore, it was found that viral infection and peptide immunization induced MAFA expression. This demonstrates that tumor-specific CTL generated in vivo express MAFA, and may also express other NK receptors.

The inhibitory effect of the monoclonal antibody 7B5 was quite dramatic. In spite of the presence of other inhibitory receptors on NK cells, 7B5 antibody alone exhibited a strong inhibitory effect on NK cell function. This demonstrates that signaling through MAFA is sufficient to inhibit the cytotoxic activity of NK cells and this is independent from other NK cell receptors such as Ly49. It should be noted that only a limited number of NK cells cultured with IL-2 were MAFA+. It is possible that only a fully-activated NK cell subset expresses MAFA. The present study also demonstrated that clustering of FcERI is not required for the induction of MAFA signaling since NK cells do not express FcERI.

It was also demonstrated that recombinant soluble MAFA augmented NK cell function. This demonstrates that the soluble MAFA interfered with the interaction between MAFA and its ligand, thus inhibiting signaling through the MAFA receptor. The possibility that soluble MAFA prevents the interaction between other C type lectin receptor(s) and their ligands cannot be excluded because MAFA is a lectin receptor and soluble MAFA does bind to glycoproteins derived from fungi. However, it is unlikely that the MAFA ligand is the same ligand as for other NK cell receptors, which have been identified as MHC Class I specific receptors, since MAFA inhibits IgE-stimulated mast cell activation, which is independent of MHC Class I interaction.

A number of embodiments of the invention have been described. Nevertheless, it will be understood that various modifications may be made without departing from the spirit and scope of the invention. Accordingly, other embodiments are within the scope of the following claims.

What is claimed is:

1. A method for inhibiting an NK- or a T cell-expressed cell surface Mast cell function associated antigen (MAFA) binding to a ligand on a target cell in vitro or ex vivo comprising the following steps
   (a) providing an anti-MAFA antibody or an antigen binding fragment thereof that specifically binds to a MAFA polypeptide set forth in any of SEQ ID NOs: 1, 3 or 5, wherein antibody binding to the MAFA polypeptide inhibits the binding of NK or T cell expressed cell surface MAFA to the ligand on the target cell; and
   (b) contacting the anti-MAFA antibody or the antigen binding fragment thereof to the NK or the T cell or the target cell in vitro or ex vivo in an amount sufficient to inhibit cell surface MAiFA binding to the ligand on the target cell.

2. The method of claim 1, wherein binding of the anti-MAFA antibody or the fragment thereof to the MAFA expressed on the NK or T cells generates an inhibitory signal to the NK or the T cell that inhibits NK cell- or T cell-mediated cytotoxicity.

* * * * *